United States Patent
Wong et al.

(10) Patent No.: US 6,767,894 B1
(45) Date of Patent: Jul. 27, 2004

(54) USE OF CILIARY NEUROTROPHIC FACTOR

(75) Inventors: Vivien W. Wong, Scarsdale, NY (US); Ellen M. Koehler-Stec, Rye Brook, NY (US); Neil Stahl, Carmel, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 09/577,468

(22) Filed: May 24, 2000

Related U.S. Application Data

(63) Continuation-in-part of application No. 09/031,693, filed on Feb. 27, 1998, now Pat. No. 6,472,178.

(51) Int. Cl.$^7$ .............................................. A61K 38/18
(52) U.S. Cl. ............................................ 514/12; 514/2
(58) Field of Search ........................................ 514/12, 2

(56) References Cited

FOREIGN PATENT DOCUMENTS

| EP | 1010432 A1 | 6/2000 |
|---|---|---|
| WO | WO91/04316 | 4/1991 |
| WO | WO91/19009 | 12/1991 |
| WO | WO98/22128 | 5/1998 |
| WO | 98/22128 | * 5/1998 |

OTHER PUBLICATIONS

Miller, R.G., et al, Annals of Neurology (1996) vol. 39,No. 2, pp. 256–260, XP008005507, "A placebo–controlled trail of recombinant human ciliary neurotrophic (rhCNTF) factor in amyotrophic lateral sclerosis."

Miller, R.G., et al, Neurology (1996), vol. 47, No. 5, pp. 1329–1331, XP001064801, "Toxicity and tolerability of recombinant human ciliary neurotrophic factor in patients with amyotrophic lateral sclerosis."

Group A.C.T.S., Neurology, issued 1996, "A double–blind placebo–controlled clinical trial of subcutaneous recombinant human ciliary neurotrophic factor (rHCNTF) in amyotrophic lateral scelrosis", pp. 1244–1249.

Gloaguen, I., et al., Proc. Natl. Acad. Sci., vol. 94, issued 1997, Ciliary neurotrophic factor corrects obesity and diabetes associated with leptin deficiency and resistance, pp. 6456–6461.

Panayotatos, N., et al., Biochemistry, vol. 33, issued 1994, "Recombinant Human CNTF Receptor α: Production, Binding Stereochemistry, and Characterization of Its Activity as a Diffusible Factor", pp. 5813–5818.

Panayotatos, N., et al., J. Biol. Chem., vol. 268, issued 1993, "Exchange of a Single Amino Acid Interconverts the Specific Activity and Gel Mobility of Human and Rat Ciliary Neurotrophic Factors", pp. 19000–19003.

Vaisse, C., et al., Nature Gen, vol. 14, issued Sep. 14, 1996, "Leptin activation of Stat3 in the hypothalamus of wild–type and ob/ob mice but not db/db mice", pp. 95–97.

* cited by examiner

Primary Examiner—Gary Kunz
Assistant Examiner—Robert C. Hayes
(74) Attorney, Agent, or Firm—Valeta Gregg, Esq.

(57) ABSTRACT

Compositions and methods for the intranasal or respiratory administration of ciliary neurotrophic factor proteins, especially in the treatment of obesity and gestational or adult onset diabetes.

7 Claims, 10 Drawing Sheets

USE OF CILIARY NEUROTROPHIC FACTOR

This application is a continuation-in-part of U.S. patent application Ser. No. 09/031,693 filed Feb. 27, 1998, now U.S. Pat. No. 6,472,178. Throughout this application, various patents and publications are referenced. This patent and all publications are hereby incorporated by reference, in their entireties, into this application.

BACKGROUND OF THE INVENTION

The present invention relates to ciliary neurotrophic factor (CNTF) and CNTF-related polypeptides useful for the treatment of neurological diseases, obesity and other diseases or disorders.

CNTF is a protein that is required for the survival of embryonic chick ciliary ganglion neurons in vitro (Manthorpe et al., 1980, J. Neurochem. 34:69–75). The ciliary ganglion is anatomically located within the orbital cavity, lying between the lateral rectus and the sheath of the optic nerve; it receives parasympathetic nerve fibers from the oculomotor nerve which innervates the ciliary muscle and sphincter pupillae.

Over the past decade, a number of biological effects have been ascribed to CNTF in addition to its ability to support the survival of ciliary ganglion neurons. CNTF is believed to induce the differentiation of bipotential glial progenitor cells in the perinatal rat optic nerve and brain (Hughes et al., 1988, Nature 335:70–73). Furthermore, it has been observed to promote the survival of embryonic chick dorsal root ganglion sensory neurons (Skaper and Varon, 1986, Brain Res. 389:39 46). In addition, CNTF supports the survival and differentiation of motor neurons, hippocampal neurons and presympathetic spinal cord neurons (Sendtner, et al., 1990, Nature 345: 440–441; Ip, et al. 1991, J. Neurosci. 11:3124–3134; Blottner, et al. 1989, Neurosci. Lett. 105:316 320).

CNTF has been cloned and synthesized in bacterial expression systems, as described by Masiakowski, et al., 1991, J. Neurosci. 57:1003–1012 and in International Publication No. WO 91/04316, published on Apr. 4, 1991, both of which are incorporated by reference in their entirety herein.

In addition to human CNTF, the corresponding rat (St öckli et al., 1989, Nature 342:920–923), and rabbit (Lin et al., 1989, J. Biol. Chem. 265:8942–8947) genes have been cloned and found to encode a protein of 200 amino acids, which share about 80% sequence identity with the human gene. Both the human and rat recombinant proteins have been expressed at exceptionally high levels (up to 70% of total protein) and purified to near homogeneity.

Despite their structural and functional similarity, recombinant human and rat CNTF differ in several respects. The biological activity of recombinant rat CNTF in supporting survival and neurite outgrowth from embryonic chick ciliary neurons in culture is four times better than that of recombinant human CNTF (rHCNTF) (Masiakowski et al., 1991, J. Neurochem. 57:1003–1012). Further, rat CNTF has a higher affinity for the human CNTF receptor than does human CNTF (Davis et al., 1991, Science 253: 59–63).

A surprising difference in the physical properties of human and rat CNTF, which are identical in size, is their different mobility on SDS gels. This difference in behavior suggests the presence of an unusual structural feature in one of the two molecules that persists even in the denatured state (Masiakowski et al., 1991, J. Neurochem. 57:1003 1012).

To better understand the physical, biochemical and pharmacological properties of rHCNTF, applicants undertook rational mutagenesis of the human and rat CNTF genes based on the different biological and physical properties of their corresponding recombinant proteins (See Masiakowski, P., et al., 1991, J. Neurochem., 57:1003 1012). Mutagenesis by genetic engineering has been used extensively in order to elucidate the structural organization of functional domains of recombinant proteins. Several different approaches have been described in the literature for carrying out deletion or substitution mutagenesis. The most successful appear to be alanine scanning mutagenesis (Cunningham and Wells 1989, Science 244: 1081–1085) and homolog-scanning mutagenesis (Cunningham et al., 1989, Science 243:1330–1336). These approaches helped identify the receptor binding domains of growth hormone and create hybrid proteins with altered binding properties to their cognate receptors.

Applicants have found that the nature of the amino acid at position 63 could greatly enhance the affinity of human CNTF for soluble CNTFRα and its biological potency in vitro (Panayotatos, N., et al., J. Biol. Chem., 1993, 268:19000–19003; Panayotatos, N., et al., Biochemistry, 1994, 33: 5813–5818).

The CNTF receptor complex contains three proteins: a specificity determining α component that directly binds to CNTF, as well as two signal transducing β components (LIFRβ and gp130) that cannot bind CNTF on their own, but are required to initiate signaling in response to CNTF. The β component of the CNTFR complex is more widely distributed throughout the body than the α component. The 3 components of the CNTFR complex are normally unassociated on the cell surface; 0CNTF induces the stepwise assembly of a complete receptor complex by first binding to CNTFR α, then engaging gp130, and finally recruiting LIFRβ. When this final step in receptor assembly occurs (heterodimerization of the β components), intracellular signaling is initiated by activating non-receptor tyrosine kinases (JAK kinases) associated with the β components. JAK kinases respond by phosphorylating each other and also tyrosine residues on the receptor cytoplasmic domains, creating phosphotyrosine docking sites for the Src homology 2 domains of STAT proteins. After their phosphorylation, bound STAT proteins dissociate from the receptor, dimerize, arid translocate to the nucleus where they bind DNA and activate transcription (reviews: Frank, D. and Greenberg, M. (1996) Perspectives on Developmental Neurobiology 4: 3–18; Stahl, N. and Yancopoulos, G. (1997) Growth factors and cytokines in health and disease 2B, 777–809). Axokine™ (rHCNTF, C17A, Q63 RΔC15) ("Ax-15") is a mutant CNTF molecule with improved physical and chemical properties, which retains the ability to interact with and activate the CNTF receptor. (Panayotatos, N., et al. (1993) J. Biol. Chem. 268: 19000–19003).

Leptin, the product of the ob gene, is secreted by adipocytes and functions as a peripheral signal to the brain to regulate food intake and energy metabolism (Zhang, et al. (1994) Nature 372: 425–431). Interestingly, leptin receptor (OB-R), a single membrane-spanning receptor, has considerable sequence similarities to gp130 (Tartaglia, L., et al. (1995) Cell 83: 1263–1271). Both CNTF and leptin each signals through the JAK/STAT pathway (Baumann, H., et al. (1996) Proc. Natl. Acad. Sci. USA 93: 8374–8378; Ghilardi, N., et al. (1996) Proc. Natl. Acad. Sci. USA 93: 6231–6235). Systemic administration of both CNTF and leptin results in induction of tis-11 (Gloaguen, I., et al. (1997) Proc. Natl. Acad. Sci. USA 94: 6456–6461) and STAT3 (Vaisse, C., et al. (1996) Nature Gen. 14: 95–97) in the hypothalamic satiety center, indicating their roles in the regulation of body weight and feeding behavior. Indeed, in a clinical trial testing the use of CNTF for treating ALS, it was found that administration of CNTF to humans reduced food intake and resulted in weight loss (Group, A. C. T. S. (1996) Neurology 46:1244–1249.).

SUMMARY OF THE INVENTION

An object of the present invention is to provide CNTF and CNTF-related proteins, collectively referred to herein as CNTF proteins, for the treatment of diseases or disorders including, but not limited to, obesity and diabetes.

A further object of the present invention is to provide a method for administering CNTF or CNTF-related proteins and maintaining biological activity. A preferred embodiment of this invention is the administration of CNTF or a CNTF related protein to the nasal or respiratory system of a mammal to produce an increase in the level of the protein in the systemic blood circulation of the mammal. A particularly preferred embodiment comprises the administration of the modified CNTF molecule, designated herein as AX-15, to the nasal passages of a patient for the treatment of obesity or diabetes.

BRIEF DESCRIPTION OF THE FIGURES

FIG. 1A. Human (SEQ ID NO:1), rat (SEQ ID NO:2), rabbit (SEQ ID NO:3), mouse (SEQ ID NO:4), and chicken (SEQ ID NO:5) (Leung, et al., 1992, Neuron 8:1045–1053) sequences. Dots indicate residues found in the human sequence. FIG. 1B. Modified CNTF molecules (186 [SEQ ID NO:6], 187 [SEQ ID NO:7], 188 [SEQ ID NO:8], 189 [SEQ ID NO:9], 192 [SEQ ID NO:10], 218 [SEQ ID NO:11], 219 [SEQ ID NO:12], 222 [SEQ ID NO:13], 223 [SEQ ID NO:14], and 228 [SEQ ID NO:15] showing human CNTF amino acid residues (dots) and rat CNTF (residues shown). The name of the purified recombinant protein corresponding to each sequence is shown on the left.

FIG. 6A—Serum insulin levels were measured in AKR/J diet-induced obese mice following treatment with vehicle, diet restriction and AX-15 (0.1 mg/kg) (PF-AX-15) or AX-15 only (0.1 mg/kg) to determine the effects of diet and/or AX-15 treatment on obesity-associated hyperinsulinemia. FIG. 6B—Serum corticosterone levels were measured in AKR/J diet induced obese mice following treatment with vehicle, diet restriction and AX-15 (0.1 mg/kg) (PF-AX-15) or AX-15 only (0.1 mg/kg).

DETAILED DESCRIPTION OF THE INVENTION

Figure 1A:
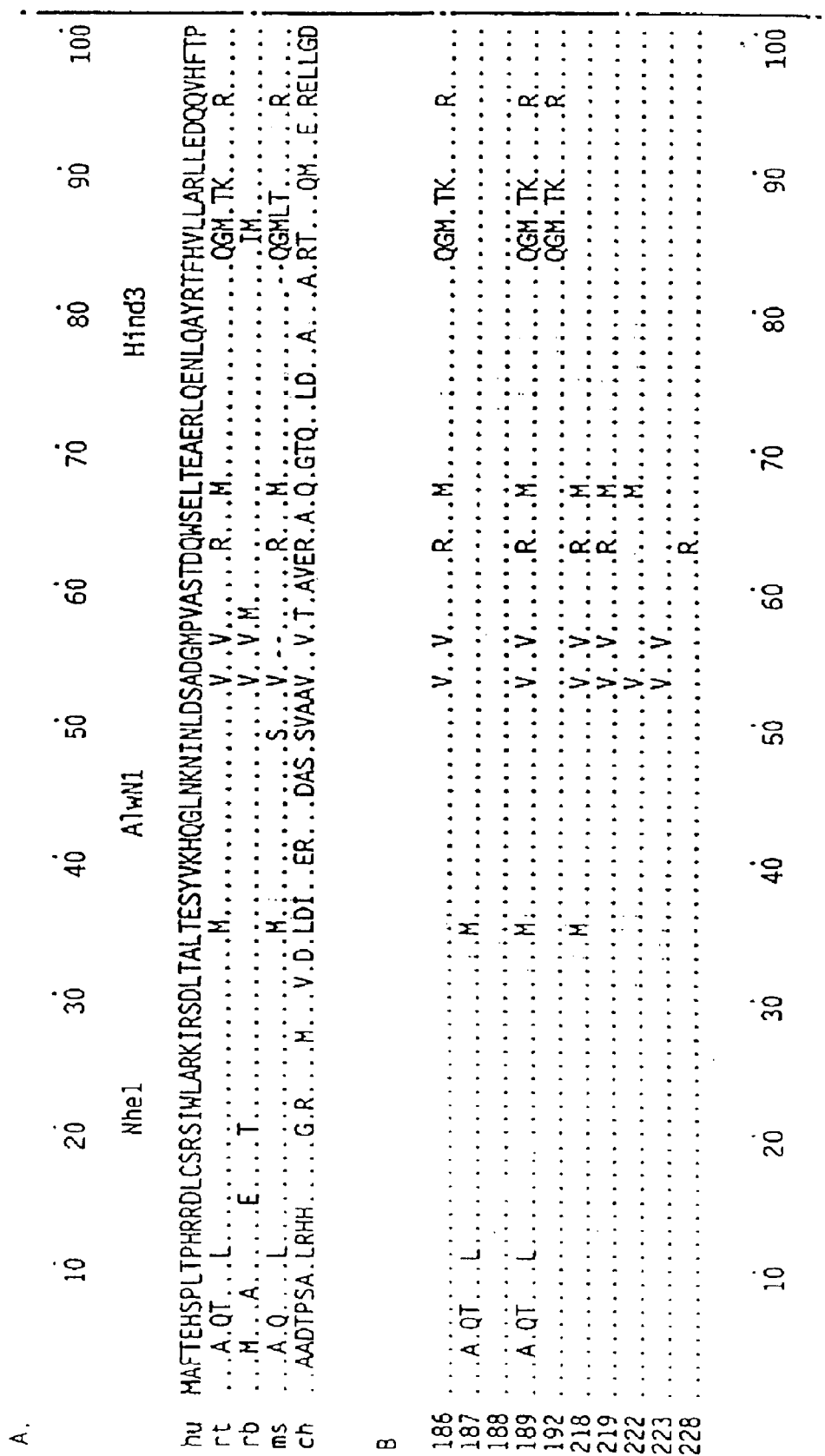
FIG. 1A and 1B—Alignment of CNTF protein sequences.

The present invention relates to a method of administering a CNTF protein to treat diseases and disorders in humans or animals.

Recombinant human and rat CNTF have the same number of amino acids (199) and similar mass (MW 22,798 and 22,721 respectively, after removal of the N-terminal methionine). Yet, on reducing SDS PAGE gels, recombinant human CNTF migrates as a protein of MW=27,500, whereas rat CNTF migrates with the expected mobility. In addition, human CNTF has four times lower biological activity towards chick ciliary ganglion (CG) neurons than rat CNTF and the human protein competes for binding to the human or the rat receptor on cell surfaces much less effectively than rat CNTF.

The above observations led to a directed effort to identify the region on the CNTF molecule responsible for these differences. This method involved the exchange, by genetic engineering methods, of parts of the human CNTF sequence with the corresponding rat CNTF sequence and vice versa. To achieve this, advantage was taken of restriction sites that are common to the two CNTF genes and unique in their corresponding expression vectors. When necessary, such sites were engineered in one or the other of the two genes in areas that encode the same protein sequence. With this approach, expression vectors were obtained for each of the modified proteins shown in FIG. 1A and 1B. After expressing and isolating the individual proteins to at least 60% purity, their properties, as compared to those of human and rat CNTF, were determined.

Because the electrophoretic mobilities of human and rat CNTF differ significantly, the effect of each amino acid substitution was monitored initially by making a determination of the effect of such change on the mobility of the protein. As described herein, electrophoretic mobility data indicated that all of the modified human CNTF molecules that migrated to the same position as rat CNTF had the single amino acid substitution Gln63Arg (Q63R), in which glutamine at position 63 is replaced with arginine.

CNTF is characterized by its capacity to support the survival of dissociated ciliary neurons of E8 chick embryos. By this criterion, purified recombinant rat CNTF is as active as the native protein from rat, but four times more active than recombinant human CNTF (Masiakowski, et al., 1991, J. Neurosci. 57:1003–1012 and in International Publication No. WO 91/04316, published on Apr. 4, 1991). The same assay was utilized to determine the biological activity of the altered molecules prepared as described above. As described herein, all modified CNTF molecules that had the Q63R substitution exhibited an increased ability to support the survival of ciliary ganglion neurons as compared to the parent human CNTF protein. Such results indicated a strong correlation between alteration electrophoretic mobility and enhanced biological properties. In addition to measuring the biological effect of modifications made to human CNTF, an indication of the potential biological activity of each of the molecules may also be obtained by determining the effect of each modification on the ability of the molecules to bind to the CNTF receptor.

As used herein, the terms "a ciliary neurotrophic factor protein", "a CNTF protein", "a ciliary neurotrophic factor molecule" and "a CNTF molecule" refer to human ciliary neurotrophic factor and modified ciliary neurotrophic factors.

As used herein, the terms "modified ciliary neurotrophic factor", "modified CNTF", "modified ciliary neurotrophic factor protein" and "modified CNTF protein" refer to CNTF proteins and polypeptides that have certain amino acid substitutions and/or deletions in the amino acid residue sequence of human CNTF which result in modified CNTF proteins and polypeptides that exhibit binding to the CNTF receptor and, therefore, would be expected to have enhanced biological, inmmunogenic and/or purification properties. CNTF proteins of the present invention may also be "pegylated" by the addition of polyethylene glycol polymers in order to enhance stability and/or bioavailability. A particularly preferred "modified ciliary neurotrophic factor" according to the invention, contains certain amino acid substitutions and deletions in the human CNTF protein and exhibits enhanced binding to the human CNTF receptor and therefore, would be expected to have enhanced biological properties, and specifically include AX-13, AX-2 and AX-15, described in more detail infra.

The CNTF molecules useful for practicing the present invention may be prepared by cloning and expression in a prokaryotic or eukaryotic expression system as described, for example in Masiakowski, et al., 1991, J. Neurosci. 57:1003–1012 and in International Publication No. WO 91/04316, published on Apr. 4, 1991. The recombinant CNTF gene may be expressed and purified utilizing any number of methods. The gene encoding this protein may be subcloned into a bacterial expression vector, such as for example, but not by way of limitation, pCP110.

The recombinant CNTF proteins may be purified by any technique which allows for the subsequent formation of a stable, biologically active protein. For example, and not by way of limitation, they may be recovered from cells either as soluble proteins or as inclusion bodies, from which they may be extracted quantitatively by 8M guanidinium hydrochloride and dialysis. Further purification of the proteins, may be done by conventional ion exchange chromatography, hydrophobic interaction chromatography, reverse phase chromatography or gel filtration.

According to the present invention, CNTF proteins produced as described herein, or hybrids or mutants thereof, may be used to promote differentiation, proliferation or survival in vitro or in vivo of cells that are responsive to CNTF, including cells that express receptors of the CNTF/IL-6/LIF receptor family, or any cells that express the appropriate signal transducing component, as described, for example, in Davis, et al., 1992, Cell 69:1121–1132. Mutants or hybrids may alternatively antagonize cell differentiation or survival.

The present invention may be used to treat disorders of any cell responsive to CNTF or the CNTF/CNTF receptor complex. In preferred embodiments of the invention, disorders of cells that express members of the CNTF/IL-6/LIF receptor family may be treated according to these methods. Examples of such disorders include, but are not limited to, obesity and diabetes.

Accordingly, the present invention provides for methods in which a patient is treated with an effective amount of the modified CNTF protein, or a hybrid or mutant thereof. The modified CNTF proteins may be utilized to treat disorders or diseases as described for CNTF in International Publication No. WO91/04316 published on Apr. 4, 1991 by Masiakowski, et al. and for the CNTF/CNTFR complex as described in International Publication No. WO91/19009 published on Dec. 12, 1991 by Davis, et al. both of which are incorporated by reference in their entirety herein.

Such diseases or disorders include degenerative diseases, such as retinal degenerations, diseases or disorders involving the spinal cord, cholinergic neurons, hippocampal neurons or diseases or disorders involving motor neurons, such as amyotrophic lateral sclerosis or those of the facial nerve, such as Bell's palsy. Other diseases or disorders that may be treated include obesity and diabetes Human clinical trials using recombinant human CNTF (rHCNTF) have been carried out wherein subcutaneous administration of the protein was tested for its efficacy in slowing the progression of amyotrophic lateral sclerosis (ALS). Such administration of rHCNTF was associated with systemic side effects, including cough, anorexia and weight loss, and, in at least one study, over 80% of patients receiving rHCNTF developed neutralizing antibodies, the significance of which is uncertain. However, despite problems with side effects and antibody formation, a subgroup of patients in the early stages of ALS appeared to derive benefit from rHCNTF administration in that these patients demonstrated a reduced rate of pulmonary function loss compared to placebo treated patients with similar disease durations. It was also found, in a clinical trial testing the use of CNTF for treating ALS, that administration of CNTF to humans reduced food intake which resulted in weight loss (Group, A. C. T. S. (1996) Neurology 46:1244–1249.).

Applicants have previously reported that rHCNTF lacking the last 13 amino acid residues from the carboxyl end (rHCNTFΔC13 also designated RPN160 or RG160) retains full biological activity and is soluble at low temperatures (5–10° C.) to at least 12 mg/ml. Yet, despite this far greater solubility, rHCNTFΔC13 precipitates in a PBS solution upon incubation at 37° C. for several hours, even at concentrations as low as 0.1 mg/ml.

It was determined that the thermal instability of rHCNTF and rHCNTFΔC13 was the result of aggregation that was initiated by intermolecular disulfide bond formation and depended strongly on protein concentration and temperature. By replacing the single cysteine residue at position 17 of human CNTF with an alanine residue, modified CNTF proteins were obtained that exhibited far greater stability and maintained their biological activity after incubation for at least 7 days in PBS at 37° C. This property is maintained in rHCNTF, Q63R variants which have higher potency due to the substitution of the glutamine residue at position 63 by arginine. In a particular example, rHCNTF, C17A, Q63R, ΔC13 (also designated RC297) shows greater biological potency than rHCNTF because of the Q63R substitution, greater solubility because of the ΔC13 deletion and greater stability because of the C17A substitution.

Applicants have also previously described the production of this modified CNTF molecule, known alternatively as AX-13 or AX-1, (designated rHCNTF, C17A, Q63RΔC13) which combines a Q63R substitution (which confers greater biological potency) with a deletion of the C-terminal 13 amino acid residues (which confers greater solubility under physiological conditions) and a C17A substitution (which confers stability, particularly under physiological conditions at 37° C.) and shows a 2–3 fold better therapeutic index than rHCNTF in an animal model. However, when expressed in E. coli, a substantial portion of the expressed protein produced is tagged with a decapeptide at the C-terminus. Because of this, purification of AX-13 is difficult and results in a low yield of purified, untagged product. This decapeptide tagging likely does not occur when the AX-13 is expressed in a mammalian expression system. In addition, it is possible that the decapeptide tag could contribute to increased immunogenicity of the molecule and may also possibly cause problems with stability. However, because the use of the E. coli expression system would be preferable from the standpoint of cost and efficiency, applicants undertook to develop a further truncated CNTF molecule that would retain the improved potency, solubility and stability properties of AX-13, while avoiding the problem of decapeptide tagging when expressed in E. coli. As described herein, applicants have succeeded in producing such a molecule designated AX-15, (rHCNTF, C17A, Q63RΔC15), which retains the improved properties of AX-13, and has an additional C-terminal truncation of two amino acids, but which also has the added advantage of being expressed by E. coli with reduced amino acid tag being added. The new molecule, AX-15, therefore has the advantage of being more easily purified with a greater yield. Another embodiment of a modified CNTF in the present invention is AX-2, which has a C17A substitution in the amino acid residue sequence of human CNTF and a truncation of the 15 C-terminal amino acid residues of human CNTF. AX-2, (rHCNTF, C17A ΔC15), differs from AX-15 solely in the absence of the Q63R substitution that is present in AX-15.

The present invention contemplates a composition comprising a ciliary neurotrophic factor protein of the invention, such as the protein described herein as AX-15, and a carrier.

Another object of the present invention is to provide a method of treating a disease or disorder comprising administering CNTF or a modified ciliary neurotrophic factor, such as the protein described herein as AX-15. The disease or disorder treated may be a degenerative disease and/or involve the spinal cord, motor neurons, cholinergic neurons or cells of the hippocampus. Alternatively, the method of treatment may be for treating a disease or disorder such as obesity or diabetes or treating a disease or disorder involving muscle atrophy.

A further object of the present invention is to provide a method of inducing weight loss in a mammal comprising administration to the mammal of a ciliary neurotrophic factor protein, particularly AX-15. A specific embodiment of this invention involves inducing weight loss in a human.

The method of administering a CNTF protein, such as AX-15, may be used in the treatment of diet induced obesity or obesity of a genetically determined origin. In a preferred embodiment, a modified CNTF protein, such as AX-15 described herein, may also be used in a method of preventing and/or treating the occurrence of gestational or adult onset diabetes in a human.

Any of the above-described methods involving the administration of CNTF or a modified CNTF, such as AX-15 described herein, may be practiced by administering the CNTF protein via a route of delivery selected from the group consisting of intravenous, intramuscular, intraocular, subcutaneous, intranasal, respiratory or intratracheal, such as by use of a nebulizer, and by intracolonic or vaginal suppositories. Alternatively, a CNTF protein, such as AX-15 described herein, may be administered via the implantation of cells that release the modified ciliary neurotrophic factor.

The present invention also provides for pharmaceutical compositions comprising CNTF or a modified CNTF protein or hybrid or mutant thereof, such as AX-15 described herein, as the sole therapeutic agent or in a complex with the CNTF receptor, in a suitable pharmacologic carrier for use in the treatment of obesity or gestational or adult onset diabetes.

The active ingredient, which may comprise CNTF or a modified CNTF should be formulated in a suitable pharmaceutical carrier for administration in vivo by any appropriate route including, but not limited to intranasal, intratracheal, by nebulizer, intraocular and oral.

As used herein, "intranasal administration" refers to delivery to the nose or nasal passageways by spray, drops, gel, inhalant or other means.

As used herein, "intratracheal administration" refers to delivery to the throat or tracheal lumen by spray, propellant, atomizer, injection or other means.

As used herein, "by nebulizer" refers to the use of any device which reduces the formulation of the present invention to a fine spray for penetration into the lungs or nasal cavities.

As used herein, "intraocular administration" refers to delivery to the eye by drop, spray, ointment or other means.

As used herein, "oral administration" refers to delivery to the mouth, esophagus or stomach by pill, capsule, solution, tablet, lozenge, powder, spray or other means.

Depending upon the mode of administration, the active ingredient may be formulated in a liquid carrier such as saline, incorporated into liposomes, microcapsules, polymer or wax-based and controlled release preparations. In preferred embodiments, modified CNTF preparations are stable solutions, or formulated into tablet, pill or capsule forms.

The concentration of the active ingredient used in the formulation will depend upon the effective dose required and the mode of administration used. The dose used should be sufficient to achieve circulating plasma concentrations of active ingredient that are efficacious. Effective doses may be extrapolated from dose-response curves derived from in vitro or animal model test systems. Effective doses are expected to be within the range of from about 0.001 to about 1 mg/day.

EXAMPLES

Example 1

Electrophoretic Mobility of Modified Human CNTF Molecules

Materials and Methods
Preparation of Modified CNTF molecules
Bacterial Strains and Plasmids E. coli K-12 RFJ26 is a strain that overproduces the lactose operon repressor.

The expression vectors pRPN33, which carries the human CNTF gene and pRPN110 which carries the rat CNTF gene are nearly identical (Masiakowski, et al., 1991, J. Neurosci. 57:1003–1012 and in International Publication No. WO 91/04316, published on Apr. 4, 1991.)

Plasmid pRPN219 was constructed by first digesting pRPN33 with the restriction enzymes Nhe1 plus Hind3 and gel purifying the 4,081 bp fragment. The second, much smaller fragment which codes for part of the human CNTF gene was subsequently replaced with an 167 bp Nhe1-Hind3 fragment that was obtained by PCR amplification from the rat gene using the primers RAT-III-dniH: 5' ACGGTAACCT TGGAGGTTCTC 3'; (SEQ ID NO: 18) and RAT-Nhe-I-M: 5' TCTATCTGCC TAGCAAGGAA GATTCGTFCA GAC- CTGACTG CTCITACG 3'.(SEQ ID NO: 19).

Plasmid pRPN228 was constructed in the same manner as pRPN219, except that the 167 bp replacement fragment was amplified using the DNA primers Rat-III-dniH-L-R: 5' AAG GTA CGA TAA GC TGG AGG TTC TCT TGG AGT CGC TCT GCC TCA GTC AGC TCA CTC CAA CGA TCA GTG 3' (SEQ ID NO:20) and Rat-Nhe-I: 5' TCT ATC TGG CTA GCA AGG AAG 3' (SEQ ID NO:21).

Figure 1B:
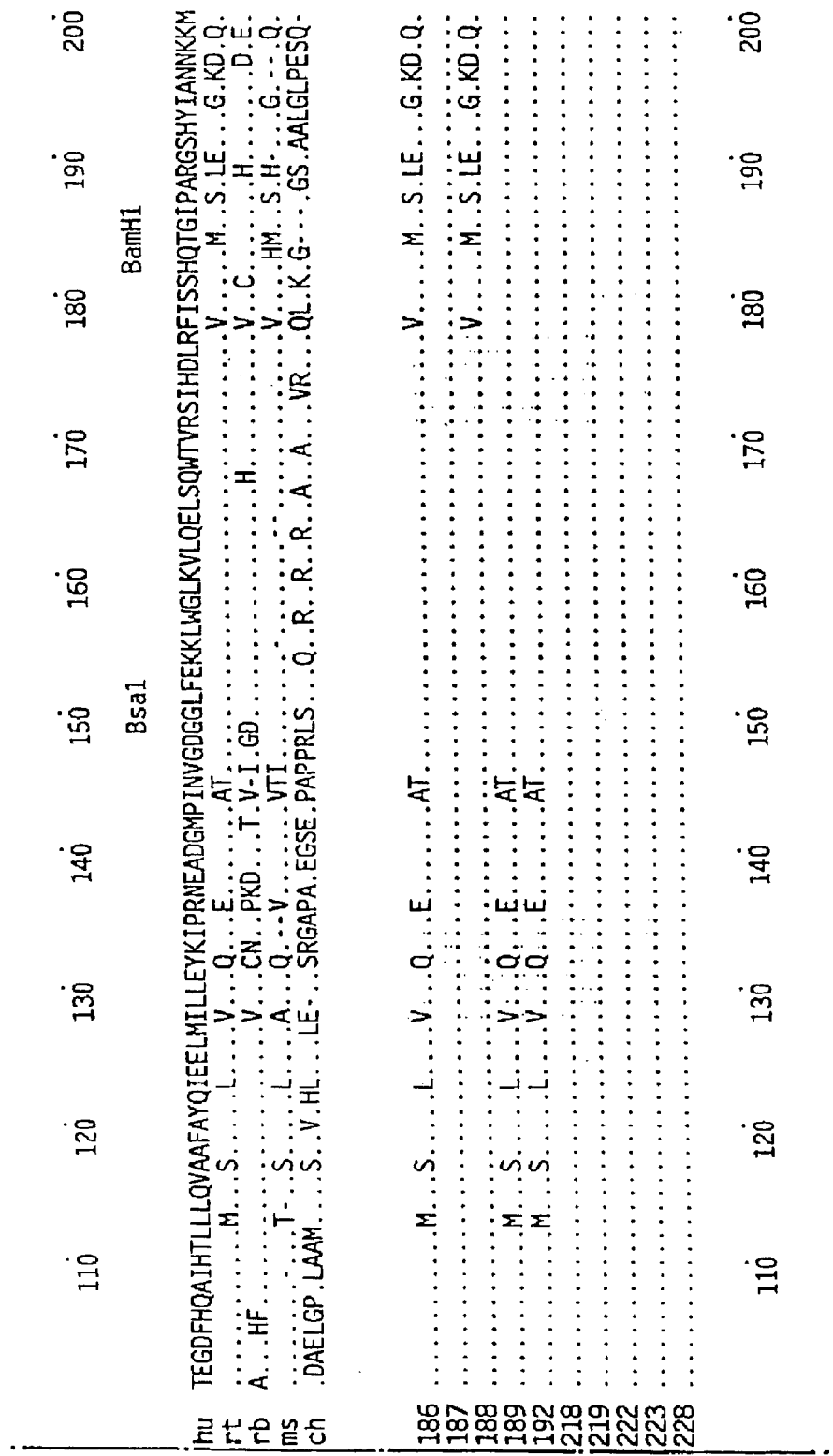

Plasmids pRPN186, pRPN187, pRPN188, pRPN189, pRPN192, pRPN218, and pRPN222 were generated by similar means or by direct exchange of DNA fragments using the unique restriction sites shown in FIGS. 1A and 1B.

The identity of all plasmids was confirmed by restriction analysis and DNA sequencing.
Protein Purification Induction of protein synthesis, selective extraction, solubilization and purification from inclusion bodies were as described for rat and human CNTF (Masiakowski, et al., 1991, J. Neurosci. 57:1003–1012 and in International Publication No. WO 91/04316, published on Apr. 4, 1991) except that gel filtration was occasionally used instead or in addition to ion exchange chromatography. Alternatively, proteins were purified from the supernatants of cell lysates by streptomycin and ammonium sulfate fractionation, followed by column chromatography, as described for other proteins (Panayotatos et al., 1989, J. Biol. Chem. 264:15066–15069). All proteins were isolated to at least 60% purity.

Figure 2:
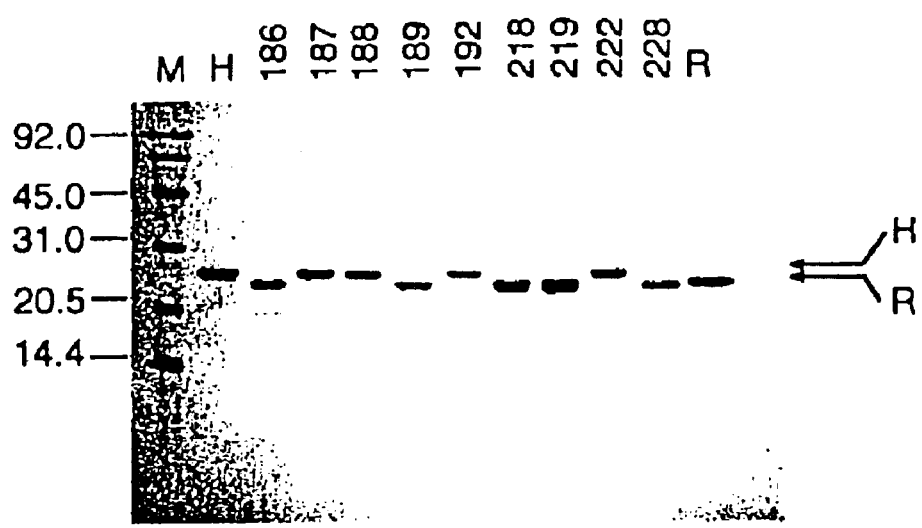
FIG. 2—Mobility of human, rat and several modified CNTF molecules on reducing SDS-15% polyacrylamide gels. Purified recombinant proteins were loaded as indicated. Markers of the indicated MW were loaded on lane M.

Conditions for enzymatic reactions, DNA electrophoresis and other techniques used in these studies have been described in detail (Panayotatos, N. 1987, Engineering an Efficient Expression System in Plasmids: A practical Approach (Hardy, K. G. ed.) pp 163–176, IRL Press, Oxford, U.K.).
Results The mobilities of human, rat and several chimeric CNTF molecules on reducing SDS-polyacrylamide gels are shown in FIG. 2. The chimeric molecules RPN186, RPN189, RPN218 and RPN228 exhibit mobilities comparable to rat CNTF, whereas RPN187, RPN188, RPN192 and RPN222 exhibit mobilities comparable to human CNTF. Cross reference of these results to the aligned sequences of these proteins in FIG. 1 reveals that all proteins carrying an arginine residue at position 63 (R63) display the mobility of rat CNTF. In the case of RPN228, a single amino acid substitution (Q63→R) is sufficient to confer to human CNTF the normal mobility of rat CNTF.

FIG. 2 also provides a measure of the purity of the different recombinant proteins. By visual inspection, purity varies from 60% for RPN189 to better than 90% for RPN228.

Example 2

Measurement of Binding Activity of Modified CNTF Molecules

Materials and Methods
Preparation of $^{125}$I-CNTF

Recombinant rat CNTF (28 mg) in 37 ml 0.2 M sodium borate buffer, pH 8.5 was transferred to a vial containing 4 mCi, (2,000 Ci/mmole; NEN) of $^{125}$I and reagent (Bolton and Hunter,1973, Biochem J. 133: 529–539) which had been dried under a gentle stream of nitrogen. Reactions were incubated for 45 min at 0° C. followed by 15 min at room temperature and terminated by the addition of 30 ml of 0.2 M glycine solution. After 15 min, 0.2 ml PBS containing 0.08% gelatin was also added and the mixture was passed through a Superdex-75™ column (Pharmacia) to separate the labeled monomeric CNTF from dimeric and other multimeric derivatives. Percentage of incorporation was typically 20%, as determined by thin layer chromatography and the specific activity was typically around 1,000 Ci/mmole. The monomeric $^{125}$I-CNTF was stored at 4° C. and used up to one week after preparation. As a test of structural and conformational integrity, $^{125}$I-CNTF (approximately 10,000 cpm) was mixed with a 5 mg unlabelled CNTF and analyzed by native gel electrophoresis. One major band was visible by either Coomassie staining or autoradiography. $^{125}$I-CNTF also showed comparable activity to native CNTF in supporting survival of E8 chick ciliary neurons in culture.
Tissue Culture Techniques Superior cervical ganglia (SCG) from neonatal rats were treated with trypsin (0.1%), mechanically dissociated and plated on a poly ornithine (30 mg/ml) substratum. Growth medium consisted of Ham's nutrient mixture F12 with 10% heat-inactivated fetal bovine serum (Hyclone), nerve growth factor (NGF) (100 ng/ml), penicillin (50 U/ml) and streptomycin (50 mg/ml). Cultures were maintained at 37° C. in a humidified 95% air/5% $CO_2$ atmosphere. Ganglion non-neuronal cells were eliminated by treatment with araC (10 mM) on days 1 and 3 of culture.

Cultures were fed 3 times/week and were routinely used for binding assays within 2 weeks.

MG87/CNTFR is a fibroblast cell line transfected with the human CNTFα receptor gene (Squinto, et al.,1990, Neuron 5:757–766; Davis et al., 1991, Science 253:59–63).
Binding Assays Binding was performed directly on cell monolayers. Cells in culture wells were washed once with assay buffer consisting of phosphate buffered saline (PBS; pH 7.4), 0.1 mM bacitracin, 1 mM PMSF, 1 mg/ml leupeptin, and 1 mg/ml BSA. After incubation with $^{125}$I-CNTF for 2 hours at room temperature, cells were quickly washed twice with assay buffer, lysed with PBS containing 1% SDS and counted in a Packard Gamma Counter. Non-specific binding was determined in the presence of 1,000-fold excess of unlabelled CNTF. Specific binding towards MG87/CNTFR was 80–90%. Data were analyzed using the GRAPHPAD program (ISI, Philadelphia, Pa.).
Results Both rat and human CNTF compete with $^{125}$I-rat CNTF for binding to SCG neurons, but human CNTF ($IC_{50}$=25 nM) is 90 times less potent in displacing $^{125}$I-rat CNTF binding than unlabelled rat CNTF ($IC_{50}$=0.28 nM). In contrast, RPN219 is almost as potent as rat CNTF and clearly more potent than human CNTF ($IC_{50}$=0.3 nM).

Similar results were obtained from competition experiments with mouse fibroblasts transfected with a plasmid directing the expression of the human CNTF receptor. Both rat, human and RPN228 compete with $^{125}$I-rat CNTF for binding to MG87/CNTFR cells. Human CNTF ($IC_{50}$=30 nM) is 12 times less potent than rat CNTF ($IC_{50}$=2.8 nM), whereas RPN228 is clearly more potent than the human protein ($IC_{50}$=5.6 nM).

Competition binding experiments with the other modified CNTF proteins shown in FIG. 1 also demonstrated that proteins having R63 displayed the biological activity of rat CNTF, whereas proteins having Q63 displayed the binding properties of human CNTF (data not shown). These results indicate that the single amino acid substitution (Q63→R) is sufficient to confer to human CNTF the receptor binding properties characteristic of rat CNTF.

Example 3

Construction of AX-15 Expression Plasmid pRG643

The expression plasmid pRG632 is a high copy plasmid that encodes ampicillin resistance and the gene for human CNTF-C17A,Q63RΔC13 (also referred to herein as either AX-1 or AX-13) with a unique Eag I restriction enzyme recognition sequence 3' to the stop codon. This plasmid was used to construct a human CNTF mutation C17A,Q63R, ΔC15 (designated AX-15) by PCR amplification of a 187 bp BseR I-Eag1 DNA fragment that incorporates the ΔC15 mutation. The 5' primer {ΔC15-5' (5'-CCAGATAGAGGAGTTAATGATACTCCT-3' [SEQ ID NO: 22])} encodes the BseR I site and the 3' primer,ΔC15-3' {(5'-GCGTCGGCCGCGGACCACGCTCATTACCCAGTCTGTGAGAAGAAATG-3'[SEQ ID NO: 23])} encodes the C-terminus of the AX-15 gene ending at Gly185 followed by two stop codons and an Eag I restriction enzyme recognition sequence. This DNA fragment was disgested with BseR I and Eag I and ligated into the same sites in pRG632. The resulting plasmid, pRG639, encodes the gene for AX-15 (human CNTF C17A,Q63R,ΔC15). The ΔC15 mutation was then transferred as a 339 bp Hind III-Eag I DNA fragment into the corresponding sites within pRG421, a high copy number expression plasmid encoding the gene for kanamycin resistance and human CNTF C17A,Q63R,ΔC13. The resulting plasmid, pRG643, encodes the gene for AX-15 under transcriptional control of the lacUV5 promoter, and confers kanamycin resistance. The AX-15 gene DNA sequence was confirmed by sequence analysis.

Example 4

PEGylation of CNTF Proteins

Pegylation of proteins has been shown to increase their in vivo potency by enhancing stability and bioavailability while minimizing immunogenicity. It is known that the properties of certain proteins can be modulated by attachment of polyethylene glycol (PEG) polymers, which increases the hydrodynamic volume of the protein and thereby slows its clearance by kidney filtration. (See e.g. Clark, R., et al., 1996, J. Biol. Chem. 271: 21969–21977). We have generated PEGylated CNTF proteins by covalently linking polyethylene glycol (PEG) to AX-13. We have also developed a purification methodology to separate different PEGylated forms of CNTF proteins from non-pegylated molecules. PEGylated AX-13 has better solubility and stability properties, at physiological pH, than unPEGylated AX-13. PEGylation has been shown to greatly enhance pharmacokinetic properties of AX-13 and would be expected to similarly enhance the properties of other CNTF proteins.

Purified AX-13 derived from *E. coli* was used for these studies. 20 kD mPEG SPA was obtained from Shearwater Polymers, Bicine from Sigma, and Tris-Glycine precast gels from Novex, Calif. A small scale reaction study was set up to determine reaction conditions. 20 kD MPEG SPA was reacted with purified AX-13 at a final concentration of 0.6 mg/ml, at 4° C. in an amine-free buffer at a pH of 8.1. Molar ratios of PEG to protein were varied and two reaction times were used. The reaction was stopped by the addition of a primary amine in large excess. Reaction products were analyzed by reducing SDS-PAGE. The predominant modified species ran at a molecular weight of approximately 60 kD. Higher order modified bands that ran at higher molecular weights were also seen. Based on this study, an overnight reaction at a PEG to protein ratio of 4 was chosen.

AX-13 at 0.6 mg/ml, was reacted with 20 kD MPEG SPA in a Bicine buffer overnight at 4° C. at a pH of 8.1. The reaction was stopped by the addition of a primary amine in large excess. The reaction product was diluted with a low salt buffer and applied to an ion-exchange column. The column was washed with a low salt buffer and eluted with a NaCl gradient. A good separation between higher order forms (apparent MW>66 kD on SDS-PAGE), a distinct pegylated species that ran at about 60 kD and unpegylated AX-13 was obtained. Fractions corresponding to the 60 kD band were tested in a bioassay. A very faint band of unpegylated AX-13 was noticed in the fractions corresponding to the 60 kD band. To ensure that the bioassay results were not influenced significantly by this material, the 60 kD band was further purified by size exclusion chromatography (SEC) that resulted in baseline separation between unpegylated AX-13 and the 60 kD band. The purified pegylated AX-13 was tested in a bioassay and the results were indistinguishable from those obtained with the material prior to SEC.

Example 5

Small Scale Expression and Purification of AX-15 Protein

*E. coli* strain RFJ141 containing pRG639 was grown in LB medium and expression of AX-15 protein was induced by the addition of lactose to 1% (w/v). Induced cells were harvested by centrifugation, resuspended in 20 mM Tris-HCl, pH 8.3, 5 mM EDTA, 1 mM DTT, and lysed by passage through a French pressure cell at 10,000 psi. The cell lysate was centrifuged and the pellet was resuspended in 8 M guanidinium-HCl, 50 mM Tris-HCl, pH 8.3, 0.05 mM EDTA then diluted with 5 volumes of 50 mM Tris-HCl, pH 8.3, 0.05 mM EDTA (Buffer A) followed by dialysis against Buffer A. The dialysate was loaded onto a Q-sepharose column equilibrated with Buffer A. The AX-15 protein was eluted by a linear gradient to 1 M NaCl in 10 column volumes of buffer. Fractions containing AX-15 were pooled and brought to 1 M $(NH_4)_2SO_4$ by the slow addition of solid $(NH_4)_2SO_4$ while maintaining the pH at 8.3 by the addition of NaOH. The pool was loaded onto a phenyl-sepharose column equilibrated with 1 M $(NH_4)_2SO_4$ in Buffer A. The column was washed with 0.5 M $(NH_4)_2SO_4$ in Buffer A, and the AX-15 protein was eluted by a linear gradient of decreasing $(NH_4)_2SO_4$ concentration. Fractions containing AX-15 protein were pooled, dialyzed against 5 mM $NaPO_4$, pH 8.3, then concentrated by ultrafiltration. The concentrated pool was fractionated on a Sephacryl S-100 column equilibrated with 5 mM NaPO4, pH 8.3.

Example 6

Large Scale Expression and Purification of AX-15 Protein

A recombinant, kanamycin resistant *E. coli* strain RFJ141 expressing the AX-15 protein under lac promoter control (pRG643) was grown to an intermediate density of 30–35 $AU_{550}$ (Absorbance @ 550 nM) in a minimal salts, glucose medium containing 20 μg/ml kanamycin. Expression of AX-15 protein was induced by addition of IPTG (isopropyl thiogalactoside) to 1.0 mM and the fermentation was continued for an additional 8 hr. AX-15 protein was expressed as insoluble inclusion bodies following IPTG induction. Post-induction, cells were harvested, cell paste concentrated, and buffer exchanged to 20 mM Tris, 1.0 mM DTT, 5.0 mM EDTA, pH 8.5 via AGT 500,000 molecular weight cut off (mwco) hollow fiber diafiltration (ACG Technologies, Inc.). Inclusion bodies were released from the harvested cells by disruption via repeated passage of cooled (0–10° C.) cell paste suspension through a continuous flow, high pressure (>8,000 psi) Niro Soavi homogenizer. The homogenate was subjected to two passages through a cooled (4–8° C.) continuous flow, high speed (>17,000×G) Sharples centrifuge (source) to recover inclusion bodies. Recovered inclusion bodies were extracted in 8.0 M guanidine HCl with 1.0 mM DTT. The AX-15 protein/guanidine solution was diluted into 50 mM Tris-HCl, 1.0 mM DTT, 0.05 mM EDTA, pH 8.0–8.3, and diafiltered versus diluent buffer with AGT 5,000 mwco hollow fiber filters (ACG Technologies, Inc.). The resulting solution, containing refolded AX-15, was filtered through a Microgon 0.22 μm hollow fiber filter (ACG Technologies, Inc.) prior to chromatographic purification.

Example 7

Column Chromatographic Purification of Refolded AX-15

The filtered AX-15 solution described above was loaded onto a 16.4 L DEAE Sepharose (Pharmacia) column at 10.9 mg/ml resin and washed with 50 L of 50 mM Tris, pH 8.0–8.3, 1.0 mM DTT, and 0.05 mM EDTA buffer. The AX-15 protein was eluted from the column with a 120 mM NaCl step in the same Tris buffer. Eluate exceeding a previously established 280 nM absorbance criteria of 40% maximum $A_{280}$ on the ascending portion of the peak and 20% of maximum $A_{280}$ on the descending portion of the peak was pooled and either stored frozen (–30° C.) or used in the next step of the purification procedure. Pooled eluted AX-15 protein was adjusted to 1.0 M ammonium sulfate by gradual addition of the solid compound, maintaining the pH at 8.0–8.3. The solution was filtered through a 0.22 μm Sartorious capsule filter, loaded onto a 12.5 L phenyl Sepharose HP (Pharmacia) column at 8.24 mg/ml of resin, and washed with 55 L of 1.0 M ammonium sulfate in 50 mM Tris buffer with 0.05 mM EDTA, pH 8.0–8.3. Following a 12.0 L wash with 250 mM ammonium sulfate in the same Tris buffer, the AX-15 protein was eluted with a 125 mM ammonium sulfate, Tris buffer wash step. Eluate exceeding previously established 280 nM absorbance criteria of 100% maximum $A_{280}$ on the ascending portion of the peak and 20% of maximum $A_280$ on the descending portion of the peak was pooled. Eluate-was simultaneously diluted 1:4 into 50 mM Tris, pH 8.0 –8.3 buffer without salt to reduce its conductivity. Pooled material was stored frozen (-30° C) or used in the following step. Pooled hydrophobic interaction chromatography (HIC) material was concentrated to 25 L and diafiltered versus 5.0 mM sodium phosphate buffer pH 8.0–8.3 using a 5,000 mwco AGT hollow fiber filter (ACG Technologies, Inc.). The pH was adjusted to 7.0–7.2 immediately prior to sulfyl propyl fast flow (SP FF) sepharose chromatography by gradual addition of concentrated (85%) phosphoric acid. The pH-adjusted pooled material was loaded onto a 7.7 L SP FF sepharose (Pharmacia) column to 9.0 mg/ml of resin and washed with a minimum of 25 L of 5.0 mM sodium phosphate buffer, pH 7.0. The AX-15 protein was eluted with a 77.0 L step of 5.0 mM sodium phosphate, 130 mM NaCl, pH 7.0–7.2. The eluate was simultaneously diluted 1:5 into 10.0 mM sodium phosphate, pH 9.0–9.2 buffer without salt to reduce conductivity and increase pH. Peak material exceeding 20% maximum $A_{280}$ on the ascending portion of the peak and 20% of the maximum $A_{280}$ on the descending portion of the peak was pooled. Pooled AX-15 protein was stored frozen (–30° C.) or used in the following step. Pooled SP FF sepharose AX-15 protein was concentrated and diafiltered versus 5.0 mM sodium phosphate, pH 8.0–8.3 buffer with a 5,000 mwco AGT hollow fiber filter (ACG Technologies, Inc.). The pool (24.66 g) was concentrated to <5.0 L. Concentrated, diafiltered AX-15 protein was loaded onto a 50 L S-100 Sephacryl (Pharmacia) sizing column and eluted with 250 L of the same 5.0 mM sodium phosphate buffer, pH 8.0–8.3. Peak material exceeding 40% maximum $A_{280}$ on the ascending portion of the peak and 40% of the maximum $A_{280}$ on the descending portion of the peak was pooled. The pooled AX-15 protein was filtered through Millipak 0.22 μm filters and stored at –80° C. prior to dispensing or formulation. The amino acid sequence of AX-15 produced follows. Alternatively, one could produce a sequence which contains a methionine residue before the initial alanine.

```
                                                              SEQ ID NO: 16
          9         19         29         39         49         59
          *          *          *          *          *          *
    AFTEHSPLT PHRRDLASRS IWLARKIRSD LTALTESYVK HQGLNKNINL DSADGMPVAS 69         79         89         99        109        111
          *          *          *          *          *          *
    TDRWSELTEA ERLQENLQAY RTFHVLLARL LEDQQVHFTP TEGDFHQAIH TLLLQVAAFA 129        139        149        159        169        179
          *          *          *          *          *          *
```

-continued
```
YQIEELMILL EYKIPRNEAD GMPINVGDGG LFEKKLWGLK VLQELSQWTV RSIHDLRFIS

*
SHQTG
```

```
                                                        SEQ ID NO: 17
METHIONINE+
         10         20         30         40         50         60
         *          *          *          *          *          *
MAFTEHSPLT PHRRDLASRS IWLARKIRSD LTALTESYVK HQGLNKNINL DSADGMPVAS 70         80         90        100        110        120
         *          *          *          *          *          *
TDRWSELTEA ERLQENLQAY RTFHVLLARL LEDQQVHFTP TEGDFHQAIH TLLLQVAAFA 130        140        150        160        170        180
         *          *          *          *          *          *
YQIEELMILL EYKIPRNEAD GMPINVGDGG LFEKKLWGLK VLQELSQWTV RSIHDLRFIS

*
SHQTG
```

Example 8

Use of AX-15 to Treat Obesity

Animal Models:

Normal mice

Normal (8 weeks) C57BL/6J mice were obtained from Taconic. The mice received daily subcutaneous injections of vehicle or AX-15. The animals were weighed daily and food intake over 24-hours was determined between days 3 and 4.

ob/ob Mice

As a result of a single gene mutation on chromosome 6, ob/ob mice produce a truncated, non-functional gene product (leptin). These mice are hyperphagic, hyperinsulinemic, and markedly obese.

C57BL/6J ob/ob mice were obtained from Jackson Laboratory and used for experiments at 12–14 weeks of age. The mice received daily subcutaneous injection of vehicle, AX-15, or leptin. Pair-fed group was given the average amount (g) of food consumed by animals treated with AX-15 (0.3 mg/kg). Body weights were obtained daily and food intake over 24-hours was determined between days 3 and 4. On day 8, the animals were sacrificed and carcass analysis was performed.

Diet-induced Obesity (DIO) Mice

AKR/J mice have been shown to be very susceptible to diet induced obesity by increasing body fat content. Although the gene environment(diet) interaction is not completely known regarding this kind of dietary obesity, like in human obesity, the genotype is polygenic.

AKR/J mice were obtained from Jackson Laboratory and put on a high fat diet (45% fat; Research Diets) at age 10–12 weeks old. All experiments commenced after 7 weeks on high fat diet. The mice received daily subcutaneous injection of vehicle, AX-15, or leptin. Pair-fed group was given the average amount (g) of food consumed by animals treated with AX-15 (0.1 mg/kg). The animals were weighed daily and food intake over 24-hours was determined between days 3 and 4. On day 8, the animals were sacrificed and sera were obtained for insulin and corticosterone measurements.

II. Reagents:

Recombinant human AX-15 was manufactured as set forth above and leptin was purchased from R & D Systems.

Results

Normal Mice

Figure 3:
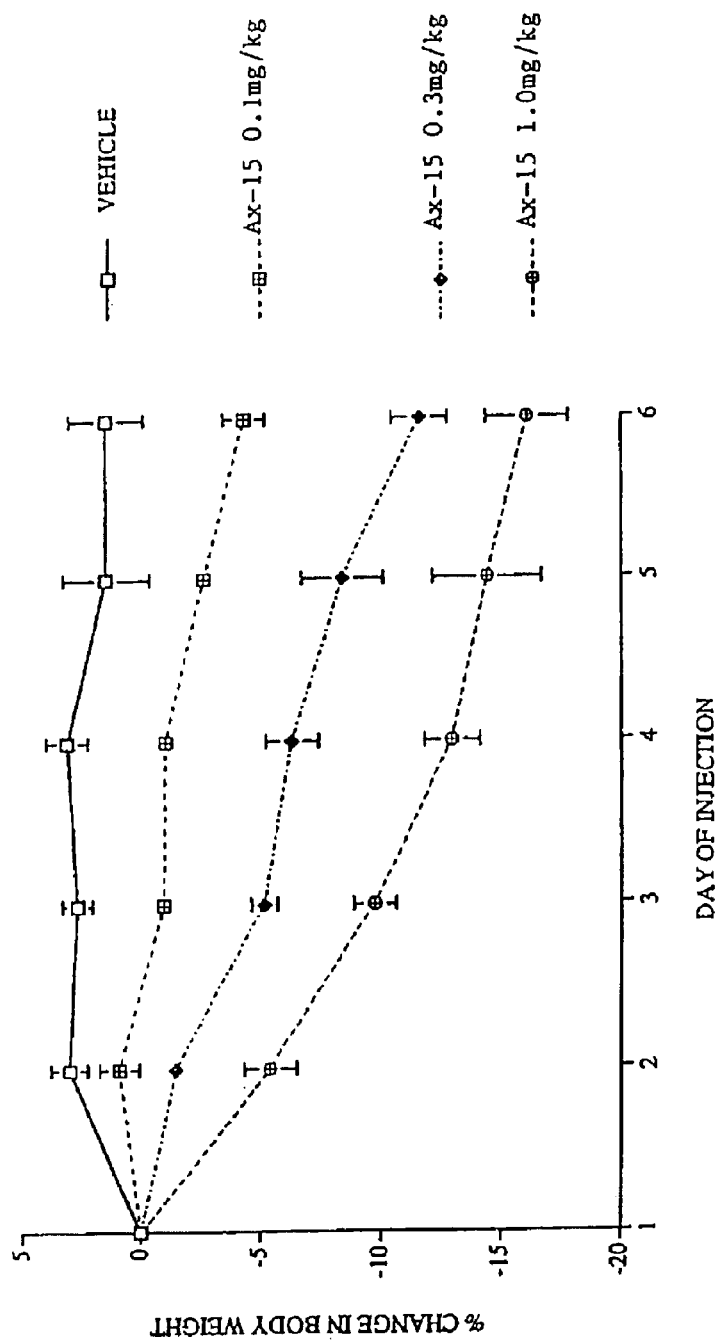
FIG. 3—Effects of Axokine[-15]™ (rHCNTF, C17A, Q63RΔC15) (AX-15) in normal mice. Normal C57BL/6J mice were injected subcutaneously daily for 6 days with either vehicle or AX-15 at 0.1 m, 0.3 mg/kg, or 1.0 mg/kg. Percent change in body weight in AX-15-treated versus vehicle-treated controls is shown.

AX-15 reduced body weight in normal mice in a dose dependent manner. In 6 days, the animals lost approximately 4%, 11%, and 16% of their body weight at 0.1 mg/kg, 0.3 mg/kg, and 1 mg/kg, respectively (FIG. 3).

ob/ob Mice

Figure 4:
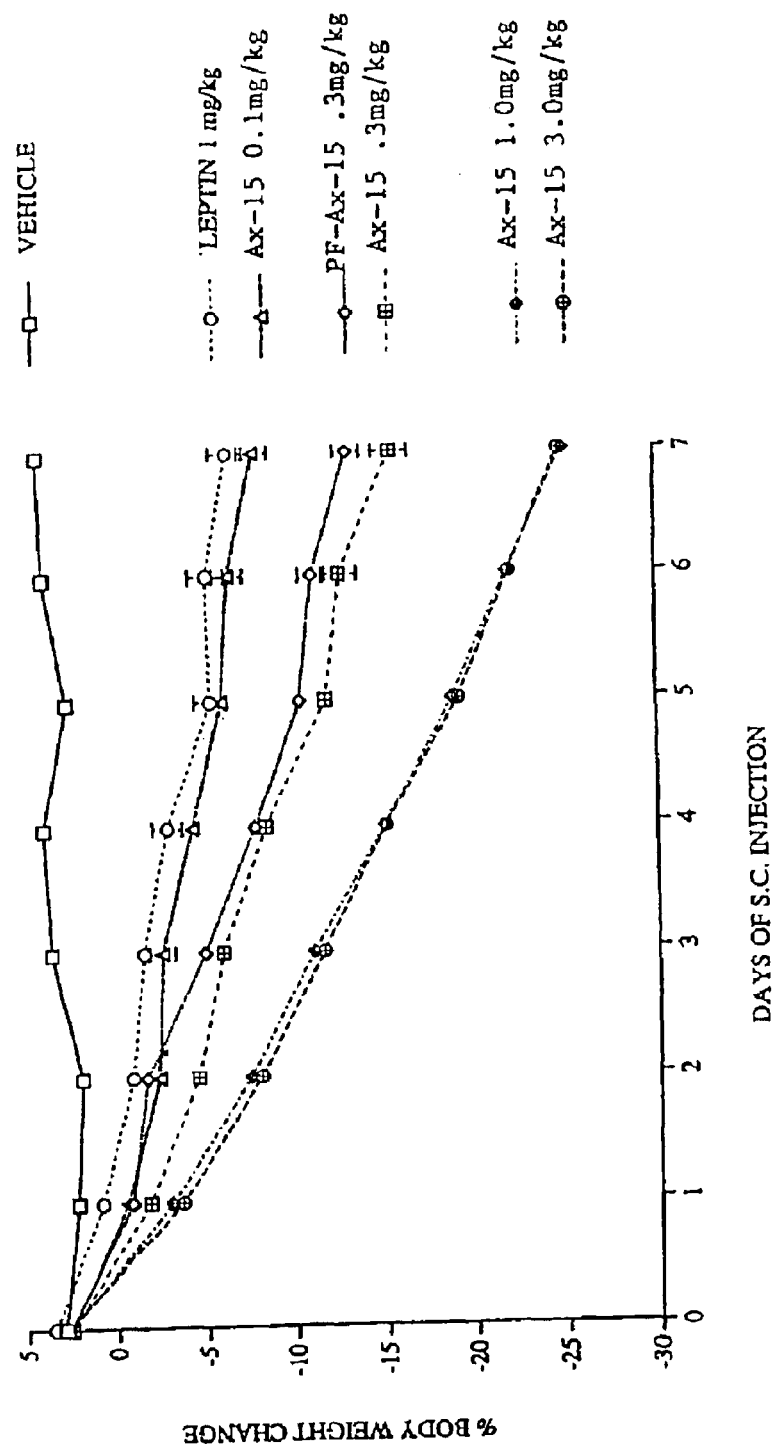
FIG. 4—Effects of AX-15 in ob/ob mice. C57BL/6J ob/ob mice were injected subcutaneously daily for 7 days with either vehicle, leptin (1.0 mg/kg) or AX-15 at 0.1 mg/kg, 0.3 mg/kg, 1.0 mg/kg or 3.0 mg/kg. Diet-restricted, pair-fed (PF) mice were injected with 0.3 mg/kg AX-15 to investigate the effects of food intake reduction on weight loss. Percent change in body weight in AX-15-treated and leptin-treated versus vehicle-treated controls is shown.

There was a dose related (0.1 mg/kg–3 mg/kg) decrease in body weight after AX-15 treatment in ob/ob mice (FIG. 4). At a dose range of 0.1 mg/kg to 3 mg/kg, there was a 8%–25% reduction of body weight. Animals pair-fed to a specific dose of AX-15 (0.3 mg/kg) showed equivalent loss of body weight as the mice given that dose of AX-15, suggesting food intake is the primary cause of weight reduction.

Leptin was also effective in decreasing body weight in ob/ob mice. At 1 mg/kg, leptin decreased body weight 6% in 7 days, following a course almost identical to that of AX-15 given at 0.1 mg/kg (FIG. 4).

Carcass analysis showed that there was a significant reduction of total body fat with AX-15 and leptin treatments as well as in pair-fed controls (Table 1). There was a small but non-significant loss of lean mass in all groups as compared to vehicle control animals. Mice receiving only food restriction (pair-fed) had a fat/lean mass ratio no different from vehicle controls, indicating that they lost fat and lean mass equally. However, the AX-15 and leptin treated animals showed preferential loss of body fat as reflected by a decrease in fat/lean mass ratio (Table 1).

DIO Mice

Figure 5:
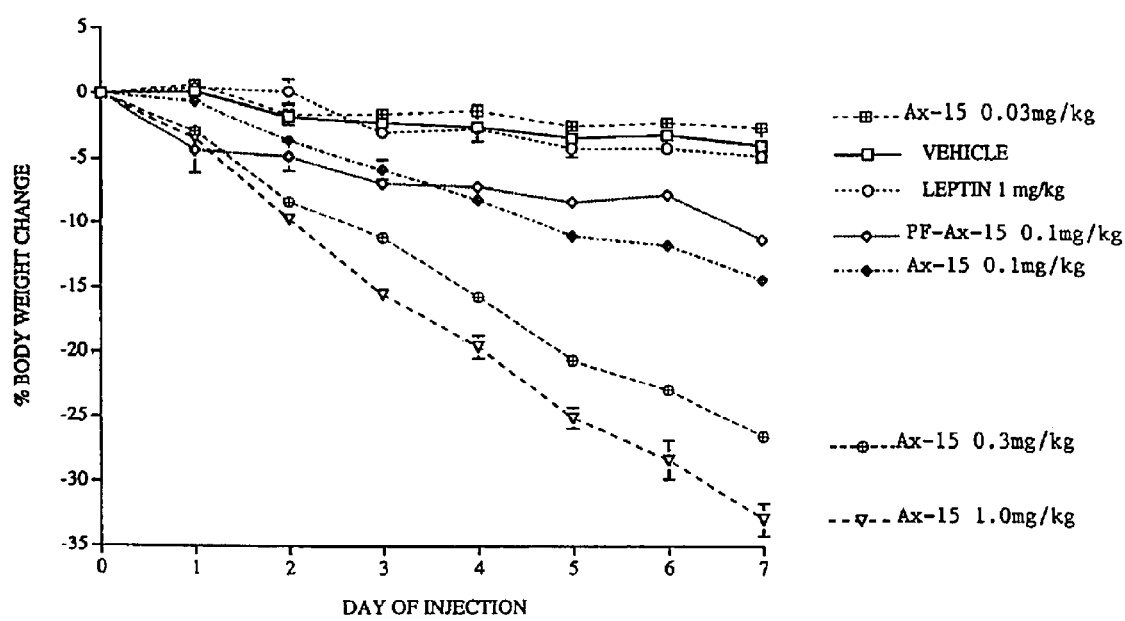
FIG. 5—Effects of AX-15 in diet-induced obesity in mice. AKR/J mice were placed on a high fat diet for seven weeks prior to treatment with vehicle, leptin (1.0 mg/kg) or AX-15 at 0.03 mg/kg, 0.1 mg/kg, 0.3 mg/kg, or 1.0 mg/kg. Diet-restricted, pair-fed AKR/J mice were injected with 0.1 mg/kg AX-15 (PF-AX-15) to investigate the effects of food intake reduction on weight loss. Percent change in body weight in AX-15 -treated and leptin-treated versus vehicle-treated controls is shown.
Figure 6A:
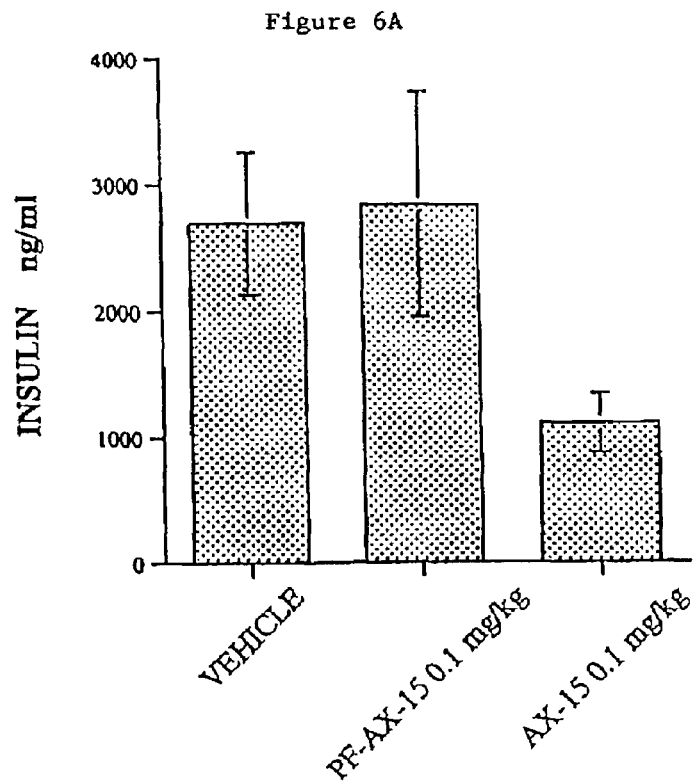
FIGS. 6A and 6B—Effects of AX-15 and diet restriction on serum insulin and corticosterone levels in diet-induced obese AKR/J mice.
Figure 6B:
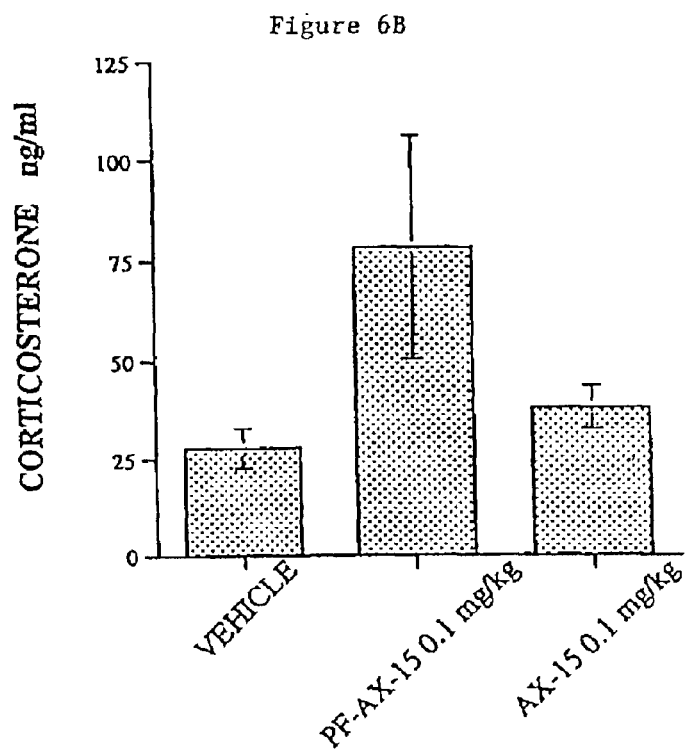

AX-15 reduced body weight in DIO mice dose dependently. Within one week, the animals lost approximately 14%, 26%, and 33% of their body weight when given AX-15 at 0.1 mg/kg, 0.3 mg/kg, and 1 mg/kg, respectively (FIG. 5). Comparing the effects of the AX-15 treatment and the pair-fed control animals, there was a small but significant difference between the 2 groups, suggesting that decrease food intake was probably the primary, although not the only, cause of weight loss with AX-15 treatment. Indeed, AX-15 significantly attenuated the obesity associated hyperinsulinemia in DIO mice, whereas merely reducing food intake (pair-fed) did not (FIG. 6A). In addition, AX-15 did not cause elevation of corticosterone levels, which is a common effect of food restriction (FIG. 6B).

It is of interest to note that when AX-15 was administered in the same dose range (0.1–1 mg/kg), DIO mice lost more than twice the body weight when compared to normal mice. This higher sensitivity of diet-induced obese animals to AX-15 suggests that adiposity may regulate the efficacy of AX-15 such that AX-15 will not cause continuous weight loss after adiposity is normalized.

DIO mice are leptin resistant; no weight loss effect was observed in these animals with daily injection of leptin (1 mg/kg; FIG. 5).

We conclude as follows:
1. AX-15 caused weight loss in normal mice in a dose dependent manner.
2. AX-15 induced weight loss in ob/ob mice in a dose dependent manner. AX-15 (0.1 mg/kg) was as effective as leptin (1 mg/kg) in causing weight loss in ob/ob mice. Both AX-15 and leptin treatments, but not pair-fed, preferentially reduced total body fat over lean mass.
3. AX-15 caused weight loss in diet-induced obesity mice in a dose dependent manner, whereas leptin was ineffective. AX-15 treatment attenuated obesity associated hyperinsulinemia in DIO mice; this effect was not observed in pair-fed control animals. In addition, AX-15 was more effective in inducing weight loss in DIO mice than normal or ob/ob mice. Taken together, our results suggest a specific useful application of AX-15 in the treatment of leptin resistant obesity, such as type II diabetes associated obesity.
4. The effectiveness of AX-15 in reducing body weight in leptin resistant mouse model suggests that AX-15 may also be effective in reducing body weight in obese humans who are resistant or unresponsive to leptin.

TABLE 1

Results from carcass analysis of ob/ob mice

|  |  | Fat g | Lean mass g | Fat:Lean Mass |
|---|---|---|---|---|
| Vehicle | Mean | 34.77 | 4.79 | 7.26 |
|  | sem | 1.41 | 0.24 |  |
| Pair-fed to Ax-15 0.3 mg/kg |  | 29.36 | 4.03 | 7.28 |
|  |  | 0.93 | 0.07 |  |
| Ax-15 0.1 mg/kg |  | 30.22 | 4.38 | 6.9 |
|  |  | 0.59 | 0.13 |  |
| Ax-15 0.3 mg/kg |  | 26.77 | 4.03 | 6.64 |
|  |  | 0.66 | 0.08 |  |
| Ax-15 1 mg/kg |  | 23.29 | 3.35 | 6.95 |
|  |  | 0.87 | 0.12 |  |
| Ax-15 3 mg/kg |  | 23 | 3.5 | 6.57 |
|  |  | 0.53 | 0.12 |  |
| Leptin 1 mg/kg |  | 28.89 | 4.73 | 6.11 |
|  |  | 0.89 | 0.1 |  |

Example 9

Intranasal Administration of AX-15

As stated above, a model of human obesity is the AKR/J mice which are susceptible to diet-induced obesity (DIO) by an increase in body fat content analogous to humans, and as in human obesity the genotype is polygenic.

Male AKR/J mice (obtained from the Jackson Laboratory, Bar Harbor, Me.) were fed a high fat diet (with 45% kcal from fat) starting at 10 weeks of age. At 17 weeks of age, they weighed about 30% more than lean littermates that were fed a normal chow diet. These mice, termed DIO mice, received daily intranasal administration of either vehicle or AX-15 (94 μg/mouse in 50 μl, which is approximately 1.87–2.35 mg/kg); n=10/group. To administer AX-15, the animals were anesthetized briefly with isofluorane, and then a drop (50 μl) of either vehicle or AX-15 was placed in their nostrils and inhaled by the animals as they breathed. A group of DIO mice receiving daily subcutaneous injection of AX-15 (0.1 mg/kg) was included as a comparison (n=5). Body weight and 24 hour food intake were recorded daily for 7 days.

A pharmacokinetics profile of AX-15 delivered by the intranasal route was determined in normal female BALB/c mice (100 μg/mouse in 50 μl, which is equivalent to 3.3 mg/kg; n=3). Sera were obtained from tail bleeds at 0, 0.5, 1, 2, 4, 8 & 24 hour intervals after injection. Levels of AX-15 were measured by a two-site ELISA, using a monoclonal antibody to CNTF as capture.

Figure 7:
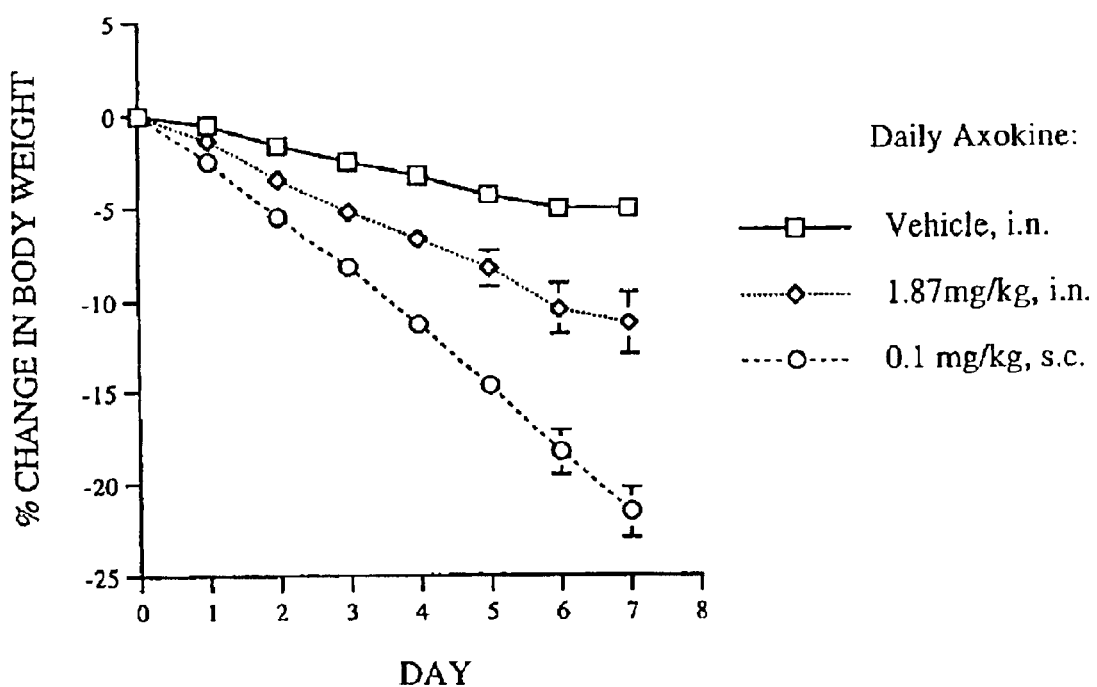
FIG. 7—Effect of intranasal delivery of AX-15 on body weight reduction in diet-induced obese AKR/J mice. DIO mice were given daily intranasal administration of either vehicle (□) or AX-15 (94 $\mu$g/mouse in 50 $\mu$l, approximately 1.87–2.35 mg/kg) ($\diamond$) for 7 days. A group of mice receiving daily subcutaneous injection of AX-15 (○) at 0.1 mg/kg was also included for comparison. The animals were weighed daily and mean body weight change was expressed as percent change from baseline +/− SEM (n=5 or 10 per group).
Figure 8:
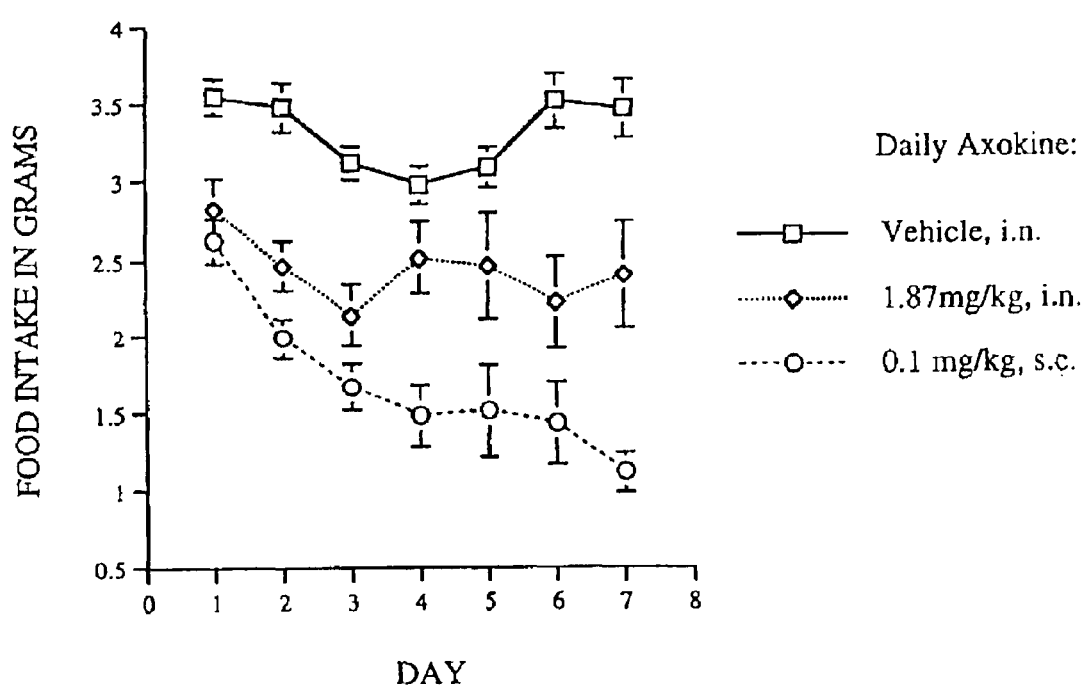
FIG. 8—Effect of intranasal delivery of AX-15 on food intake in diet-induced obese AKR/J mice. DIO mice were given daily intranasal administration of either vehicle (□) or AX-15 (94 $\mu$g/mouse in 50 $\mu$l, approximately 1.87–2.35 mg/kg) ($\diamond$) for 7 days. A group of mice receiving daily subcutaneous injection of AX-15 (○) at 0.1 mg/kg was also included for comparison. Food consumed by individual animals was determined daily and expressed as mean +/− SEM (n=5 or 10 per group).

The treatment with AX-15 via intranasal route of delivery was effective in reducing body weight in DIO mice (FIG. 7). AX-15 given daily at 94 μg/mouse caused an 11% weight loss after 7 days. Weight loss was closely correlated to decreased food intake (FIG. 8). As expected from the results in Example 8, subcutaneously administered AX-15 at 0.1 mg/kg caused a typical 21% weight loss with concomitant decrease in food consumption (FIG. 8).

Figure 9:
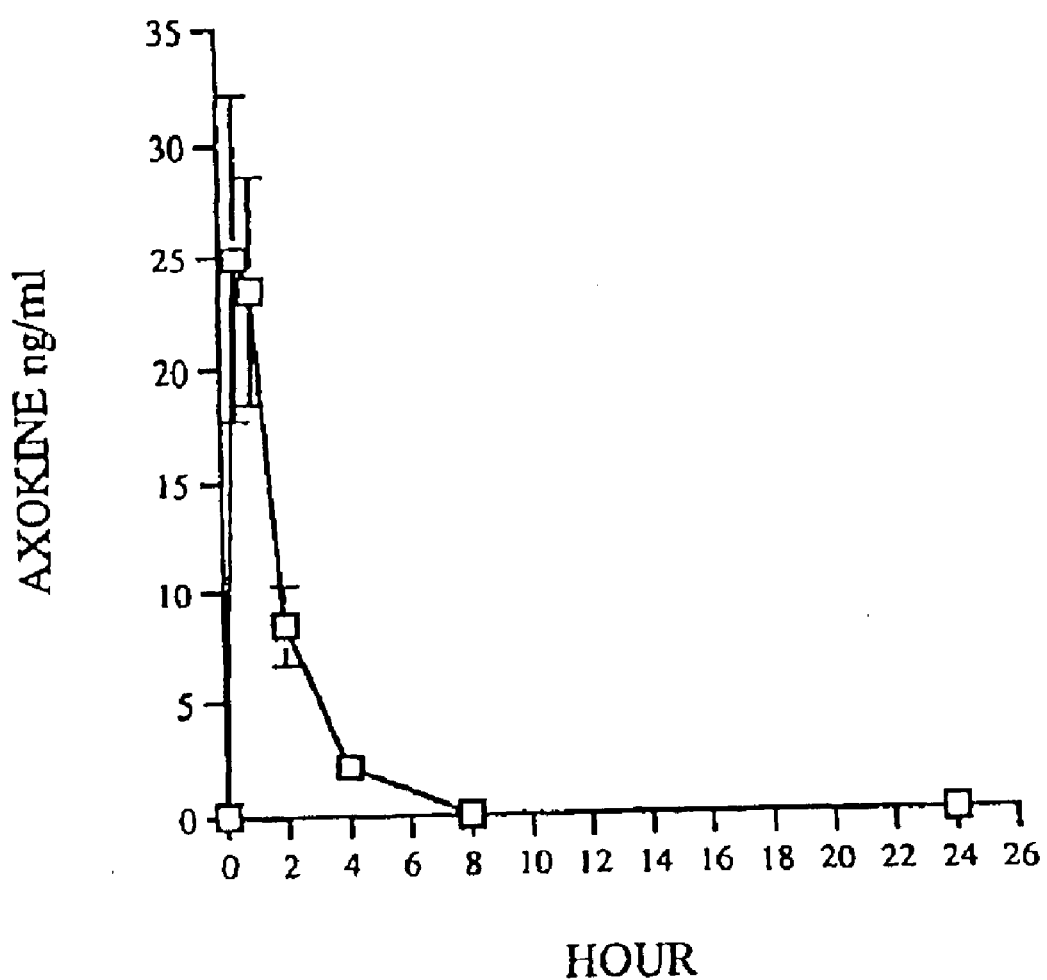
FIG. 9—Pharmacokinetic profile of AX-15 administered via intranasal route. Pharmacokinetics of AX-15 delivered by intranasal administration was determined in female BALB/c mice (100 $\mu$g/mouse in 50 $\mu$l, equivalent to 3.3 mg/kg; n=3). Sera were obtained from tail bleeds at 0, 0.5, 1, 2, 4, 8, and 24 hour intervals after administration. Levels of AX-15 were measured by a 2-site ELISA, using a monoclonal antibody to CNTF as capture.

Pharmacokinetic data showed that when AX-15 was administered by intranasal route at 3.3 mg/kg (100 μg/mouse in 50 μl), a peak serum level of 20 ng/ml (Cmax) was achieved at 0.5 –1 hour (FIG. 9). This serum level was well within the efficacious range reached when AX-15 was given by subcutaneous injection (8–25 ng/ml).

Thus, AX-15 administered via the intranasal route can be absorbed within the airway and/or through the mucosal lining of the nasal and respiratory tract and achieve serum levels that are in the efficacious range, based upon comparison to levels achieved following subcutaneous injection. AX-15 delivered via an intranasal route was effective in reducing body weight and food intake in DIO mice. Therefore, intranasal delivery can effectively be utilized as a route of administration for AX-15 in treating appropriate disorders such as obesity and diabetes.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

We claim:

1. A method of including weight loss in a mammal comprising administering a ciliary neurotrophic factor comprising the sequence of SEQ ID NO:16 or 17, wherein the administration is via the nasal or the respiratory passages of said mammal.

2. The method of claim 1, wherein the mammal is a human.

3. The method of claim 2, wherein excess weight is due to diet induced obesity.

4. The method of claim 2, wherein said ciliary neurotrophic factor protein is Axokine™ (rHCNTF, C17A, Q63RΔC15)(AX-15).

5. The method of claim 1, wherein said ciliary neurotrophic factor protein is pegylated.

6. The method of claim 1, wherein said ciliary neurotrophic factor protein is administered intranasally.

7. The method of claim 1, wherein said ciliary neurotrophic factor protein is administered by use of a nebulizer.

* * * * *

UNITED STATES PATENT AND TRADEMARK OFFICE
CERTIFICATE OF CORRECTION

PATENT NO. : 6,767,894 B1
DATED : July 27, 2004
INVENTOR(S) : Wong et al.

It is certified that error appears in the above-identified patent and that said Letters Patent is hereby corrected as shown below:

Column 41,
Line 1, after "method of" delete "including" and insert -- inducing --.

Signed and Sealed this

Twelfth Day of April, 2005

JON W. DUDAS
*Director of the United States Patent and Trademark Office*

SEQUENCE LISTING

<160> NUMBER OF SEQ ID NOS: 23

<210> SEQ ID NO 1
<211> LENGTH: 200
<212> TYPE: PRT
<213> ORGANISM: Homo sapiens

<400> SEQUENCE: 1

Met Ala Phe Thr Glu His Ser Pro Leu Thr Pro His Arg Arg Asp Leu
1               5                   10                  15

Cys Ser Arg Ser Ile Trp Leu Ala Arg Lys Ile Arg Ser Asp Leu Thr
            20                  25                  30

Ala Leu Thr Glu Ser Tyr Val Lys His Gln Gly Leu Asn Lys Asn Ile
        35                  40                  45

Asn Leu Asp Ser Ala Asp Gly Met Pro Val Ala Ser Thr Asp Gln Trp
    50                  55                  60

Ser Glu Leu Thr Glu Ala Glu Arg Leu Gln Glu Asn Leu Gln Ala Tyr
65                  70                  75                  80

Arg Thr Phe His Val Leu Leu Ala Arg Leu Leu Glu Asp Gln Gln Val
                85                  90                  95

His Phe Thr Pro Thr Glu Gly Asp Phe His Gln Ala Ile His Thr Leu
            100                 105                 110

Leu Leu Gln Val Ala Ala Phe Ala Tyr Gln Ile Glu Glu Leu Met Ile
        115                 120                 125

Leu Leu Glu Tyr Lys Ile Pro Arg Asn Glu Ala Asp Gly Met Pro Ile
    130                 135                 140

Asn Val Gly Asp Gly Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
                165                 170                 175

Arg Phe Ile Ser Ser His Gln Thr Gly Ile Pro Ala Arg Gly Ser His
            180                 185                 190

Tyr Ile Ala Asn Asn Lys Lys Met
        195                 200

<210> SEQ ID NO 2
<211> LENGTH: 200
<212> TYPE: PRT
<213> ORGANISM: Rattus norvegicus

<400> SEQUENCE: 2

Met Ala Phe Ala Glu Gln Thr Pro Leu Thr Leu His Arg Arg Asp Leu
1               5                   10                  15

Cys Ser Arg Ser Ile Trp Leu Ala Arg Lys Ile Arg Ser Asp Leu Thr
            20                  25                  30

Ala Leu Met Glu Ser Tyr Val Lys His Gln Gly Leu Asn Lys Asn Ile
        35                  40                  45

Asn Leu Asp Ser Val Asp Gly Val Pro Val Ala Ser Thr Asp Arg Trp
    50                  55                  60

Ser Glu Met Thr Glu Ala Glu Arg Leu Gln Glu Asn Leu Gln Ala Tyr
65                  70                  75                  80

Arg Thr Phe Gln Gly Met Leu Thr Lys Leu Leu Glu Asp Gln Arg Val
                85                  90                  95

His Phe Thr Pro Thr Glu Gly Asp Phe His Gln Ala Ile His Thr Leu
            100                 105                 110

Met Leu Gln Val Ser Ala Phe Ala Tyr Gln Leu Glu Glu Leu Met Val
        115                 120                 125

Leu Leu Glu Gln Lys Ile Pro Glu Asn Glu Ala Asp Gly Met Pro Ala
    130                 135                 140

Thr Val Gly Asp Gly Gly Leu Phe Glu Lys Lys Leu Trp Gly Leu Lys
145                 150                 155                 160

```
Val Leu Gln Glu Leu Ser Gln Trp Thr Val Arg Ser Ile His Asp Leu
                165                 170                 175

Arg Val Ile Ser Ser His Gln Met Gly Ile Ser Ala Leu Glu Ser His
            180                 185                 190

Tyr Gly Ala Lys Asp Lys Gln Met
        195                 200

<210> SEQ ID NO 3
<211> LENGTH: 199
<212> TYPE: PRT
<213> ORGANISM: Oryctolagus cuniculus

<400> SEQUENCE: 3

Met Ala Phe Met Glu His Ser Ala Leu Thr Pro His Arg Arg Glu Leu
  1               5                  10                  15

Cys Ser Arg Thr Ile Trp Leu Ala Arg Lys Ile Arg Ser Asp Leu Thr
                 20                  25                  30

Ala Leu Thr Glu Ser Tyr Val Lys His Gln Gly Leu Asn Lys Asn Ile
             35                  40                  45

Asn Leu Asp Ser Val Asp Gly Val Pro Met Ala Ser Thr Asp Gln Trp
 50                  55                  60

Ser Glu Leu Thr Glu Ala Glu Arg Leu Gln Glu Asn Leu Gln Ala Tyr
 65                  70                  75                  80

Arg Thr Phe His Ile Met Leu Ala Arg Leu Leu Glu Asp Gln Gln Val
                 85                  90                  95

His Phe Thr Pro Ala Glu Gly Asp Phe His Gln Ala Ile His Thr Leu
            100                 105                 110

Leu Leu Gln Val Ala Ala Phe Ala Tyr Gln Ile Glu Glu Leu Met Val
            115                 120                 125

Leu Leu Glu Cys Asn Ile Pro Pro Lys Asp Ala Asp Gly Thr Pro Val
            130                 135                 140

Ile Gly Gly Asp Gly Leu Phe Glu Lys Lys Leu Trp Gly Leu Lys Val
145                 150                 155                 160

Leu Gln Glu Leu Ser His Trp Thr Val Arg Ser Ile His Asp Leu Arg
                165                 170                 175

Val Ile Ser Cys His Gln Thr Gly Ile Pro Ala His Gly Ser His Tyr
            180                 185                 190

Ile Ala Asn Asp Lys Glu Met
        195

<210> SEQ ID NO 4
<211> LENGTH: 198
<212> TYPE: PRT
<213> ORGANISM: Mus musculus

<400> SEQUENCE: 4

Met Ala Phe Ala Glu Gln Ser Pro Leu Thr Leu His Arg Arg Asp Leu
  1               5                  10                  15

Cys Ser Arg Ser Ile Trp Leu Ala Arg Lys Ile Arg Ser Asp Leu Thr
                 20                  25                  30

Ala Leu Met Glu Ser Tyr Val Lys His Gln Gly Leu Asn Lys Asn Ile
             35                  40                  45

Ser Leu Asp Ser Val Asp Gly Val Pro Val Ala Ser Thr Asp Arg Trp
 50                  55                  60

Ser Glu Met Thr Glu Ala Glu Arg Leu Gln Glu Asn Leu Gln Ala Tyr
 65                  70                  75                  80
```

```
Arg Thr Phe Gln Gly Met Leu Thr Lys Leu Leu Glu Asp Gln Arg Val
                85                  90                  95

His Phe Thr Pro Thr Glu Gly Asp Phe His Gln Ala Ile His Thr Leu
                100                 105                 110

Thr Leu Gln Val Ser Ala Phe Ala Tyr Gln Leu Glu Glu Leu Met Ala
                115                 120                 125

Leu Leu Glu Gln Lys Val Pro Glu Lys Glu Ala Asp Gly Met Pro Val
            130                 135                 140

Thr Ile Gly Asp Gly Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
                165                 170                 175

Arg Val Ile Ser Ser His His Met Gly Ile Ser Ala His Glu Ser His
                180                 185                 190

Tyr Gly Ala Lys Gln Met
            195
```

<210> SEQ ID NO 5
<211> LENGTH: 195
<212> TYPE: PRT
<213> ORGANISM: Gallus gallus

<400> SEQUENCE: 5

```
Met Ala Ala Ala Asp Thr Pro Ser Ala Thr Leu Arg His His Asp Leu
1               5                   10                  15

Cys Ser Arg Gly Ile Arg Leu Ala Arg Lys Met Arg Ser Asp Val Thr
                20                  25                  30

Asp Leu Leu Asp Ile Tyr Val Glu Arg Gln Gly Leu Asp Ala Ser Ile
                35                  40                  45

Ser Val Ala Ala Val Asp Gly Val Pro Thr Ala Ala Val Glu Arg Trp
            50                  55                  60

Ala Glu Gln Thr Gly Thr Gln Arg Leu Leu Asp Asn Leu Ala Ala Tyr
65                  70                  75                  80

Arg Ala Phe Arg Thr Leu Leu Ala Gln Met Leu Glu Glu Gln Arg Glu
                85                  90                  95

Leu Leu Gly Asp Thr Asp Ala Glu Leu Gly Pro Ala Leu Ala Ala Met
                100                 105                 110

Leu Leu Gln Val Ser Ala Phe Val Tyr His Leu Glu Glu Leu Leu Glu
                115                 120                 125

Leu Glu Ser Arg Gly Ala Pro Ala Glu Glu Gly Ser Glu Pro Pro Ala
            130                 135                 140

Pro Pro Arg Leu Ser Leu Phe Glu Gln Lys Leu Arg Gly Leu Arg Val
145                 150                 155                 160

Leu Arg Glu Leu Ala Gln Trp Ala Val Arg Ser Val Arg Asp Leu Arg
                165                 170                 175

Gln Leu Ser Lys His Gly Pro Gly Ser Gly Ala Ala Leu Gly Leu Pro
                180                 185                 190

Glu Ser Gln
        195
```

<210> SEQ ID NO 6
<211> LENGTH: 200
<212> TYPE: PRT
<213> ORGANISM: Artificial Sequence
<220> FEATURE:
<223> OTHER INFORMATION: Modified CNTF

```
<400> SEQUENCE: 6

Met Ala Phe Thr Glu His Ser Pro Leu Thr Pro His Arg Arg Asp Leu
 1               5                  10                  15

Cys Ser Arg Ser Ile Trp Leu Ala Arg Lys Ile Arg Ser Asp Leu Thr
            20                  25                  30

Ala Leu Thr Glu Ser Tyr Val Lys His Gln Gly Leu Asn Lys Asn Ile
        35                  40                  45

Asn Leu Asp Ser Val Asp Gly Val Pro Val Ala Ser Thr Asp Arg Trp
    50                  55                  60

Ser Glu Met Thr Glu Ala Glu Arg Leu Gln Glu Asn Leu Gln Ala Tyr
65                  70                  75                  80

Arg Thr Phe Gln Gly Met Leu Thr Lys Leu Leu Glu Asp Gln Arg Val
                85                  90                  95

His Phe Thr Pro Thr Glu Gly Asp Phe His Gln Ala Ile His Thr Leu
            100                 105                 110

Met Leu Gln Val Ser Ala Phe Ala Tyr Gln Leu Glu Glu Leu Met Val
        115                 120                 125

Leu Leu Glu Gln Lys Ile Pro Glu Asn Glu Ala Asp Gly Met Pro Ala
    130                 135                 140

Thr Val Gly Asp Gly Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
                165                 170                 175

Arg Val Ile Ser Ser His Gln Met Gly Ile Ser Ala Leu Glu Ser His
            180                 185                 190

Tyr Gly Ala Lys Asp Lys Gln Met
        195                 200

<210> SEQ ID NO 7
<211> LENGTH: 200
<212> TYPE: PRT
<213> ORGANISM: Artificial Sequence
<220> FEATURE:
<223> OTHER INFORMATION: Modified CNTF

<400> SEQUENCE: 7

Met Ala Phe Ala Glu Gln Thr Pro Leu Thr Leu His Arg Arg Asp Leu
 1               5                  10                  15

Cys Ser Arg Ser Ile Trp Leu Ala Arg Lys Ile Arg Ser Asp Leu Thr
            20                  25                  30

Ala Leu Met Glu Ser Tyr Val Lys His Gln Gly Leu Asn Lys Asn Ile
        35                  40                  45

Asn Leu Asp Ser Ala Asp Gly Met Pro Val Ala Ser Thr Asp Gln Trp
    50                  55                  60

Ser Glu Leu Thr Glu Ala Glu Arg Leu Gln Glu Asn Leu Gln Ala Tyr
65                  70                  75                  80

Arg Thr Phe His Val Leu Leu Ala Arg Leu Leu Glu Asp Gln Gln Val
                85                  90                  95

His Phe Thr Pro Thr Glu Gly Asp Phe His Gln Ala Ile His Thr Leu
            100                 105                 110

Leu Leu Gln Val Ala Ala Phe Ala Tyr Gln Ile Glu Glu Leu Met Ile
        115                 120                 125

Leu Leu Glu Tyr Lys Ile Pro Arg Asn Glu Ala Asp Gly Met Pro Ile
    130                 135                 140
```

```
Asn Val Gly Asp Gly Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
                165                 170                 175

Arg Phe Ile Ser Ser His Gln Thr Gly Ile Pro Ala Arg Gly Ser His
            180                 185                 190

Tyr Ile Ala Asn Asn Lys Lys Met
        195                 200

<210> SEQ ID NO 8
<211> LENGTH: 200
<212> TYPE: PRT
<213> ORGANISM: Artificial Sequence
<220> FEATURE:
<223> OTHER INFORMATION: Modified CNTF

<400> SEQUENCE: 8

Met Ala Phe Thr Glu His Ser Pro Leu Thr Pro His Arg Arg Asp Leu
1               5                   10                  15

Cys Ser Arg Ser Ile Trp Leu Ala Arg Lys Ile Arg Ser Asp Leu Thr
                20                  25                  30

Ala Leu Thr Glu Ser Tyr Val Lys His Gln Gly Leu Asn Lys Asn Ile
            35                  40                  45

Asn Leu Asp Ser Ala Asp Gly Met Pro Val Ala Ser Thr Asp Gln Trp
50                  55                  60

Ser Glu Leu Thr Glu Ala Glu Arg Leu Gln Glu Asn Leu Gln Ala Tyr
65                  70                  75                  80

Arg Thr Phe His Val Leu Leu Ala Arg Leu Leu Glu Asp Gln Gln Val
                85                  90                  95

His Phe Thr Pro Thr Glu Gly Asp Phe His Gln Ala Ile His Thr Leu
                100                 105                 110

Leu Leu Gln Val Ala Ala Phe Ala Tyr Gln Ile Glu Glu Leu Met Ile
            115                 120                 125

Leu Leu Glu Tyr Lys Ile Pro Arg Asn Glu Ala Asp Gly Met Pro Ile
130                 135                 140

Asn Val Gly Asp Gly Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
                165                 170                 175

Arg Val Ile Ser Ser His Gln Met Gly Ile Ser Ala Leu Glu Ser His
            180                 185                 190

Tyr Glu Ala Lys Asp Lys Gln Met
        195                 200

<210> SEQ ID NO 9
<211> LENGTH: 200
<212> TYPE: PRT
<213> ORGANISM: Artificial Sequence
<220> FEATURE:
<223> OTHER INFORMATION: Modified CNTF

<400> SEQUENCE: 9

Met Ala Phe Ala Glu Gln Thr Pro Leu Thr Leu His Arg Arg Asp Leu
1               5                   10                  15

Cys Ser Arg Ser Ile Trp Leu Ala Arg Lys Ile Arg Ser Asp Leu Thr
                20                  25                  30

Ala Leu Met Glu Ser Tyr Val Lys His Gln Gly Leu Asn Lys Asn Ile
            35                  40                  45
```

```
Asn Leu Asp Ser Val Asp Gly Val Pro Val Ala Ser Thr Asp Arg Trp
    50                  55                  60

Ser Glu Met Thr Glu Ala Glu Arg Leu Gln Glu Asn Leu Gln Ala Tyr
 65                  70                  75                  80

Arg Thr Phe Gln Gly Met Leu Thr Lys Leu Leu Glu Asp Gln Arg Val
                 85                  90                  95

His Phe Thr Pro Thr Glu Gly Asp Phe His Gln Ala Ile His Thr Leu
            100                 105                 110

Met Leu Gln Val Ser Ala Phe Ala Tyr Gln Leu Glu Glu Leu Met Val
            115                 120                 125

Leu Leu Glu Gln Lys Ile Pro Glu Asn Glu Ala Asp Gly Met Pro Ala
            130                 135                 140

Thr Val Gly Asp Gly Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
                165                 170                 175

Arg Phe Ile Ser Ser His Gln Thr Gly Ile Pro Ala Arg Gly Ser His
            180                 185                 190

Tyr Ile Ala Asn Asn Lys Lys Met
            195                 200

<210> SEQ ID NO 10
<211> LENGTH: 200
<212> TYPE: PRT
<213> ORGANISM: Artificial Sequence
<220> FEATURE:
<223> OTHER INFORMATION: Modified CNTF

<400> SEQUENCE: 10

Met Ala Phe Thr Glu His Ser Pro Leu Thr Pro His Arg Arg Asp Leu
  1               5                  10                  15

Cys Ser Arg Ser Ile Trp Leu Ala Arg Lys Ile Arg Ser Asp Leu Thr
                 20                  25                  30

Ala Leu Thr Glu Ser Tyr Val Lys His Gln Gly Leu Asn Lys Asn Ile
             35                  40                  45

Asn Leu Asp Ser Ala Asp Gly Met Pro Val Ala Ser Thr Asp Gln Trp
    50                  55                  60

Ser Glu Leu Thr Glu Ala Glu Arg Leu Gln Glu Asn Leu Gln Ala Tyr
 65                  70                  75                  80

Arg Thr Phe Gln Gly Met Leu Thr Lys Leu Leu Glu Asp Gln Arg Val
                 85                  90                  95

His Phe Thr Pro Thr Glu Gly Asp Phe His Gln Ala Ile His Thr Leu
            100                 105                 110

Met Leu Gln Val Ser Ala Phe Ala Tyr Gln Leu Glu Glu Leu Met Val
            115                 120                 125

Leu Leu Glu Gln Lys Ile Pro Glu Asn Glu Ala Asp Gly Met Pro Ala
            130                 135                 140

Thr Val Gly Asp Gly Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
                165                 170                 175

Arg Phe Ile Ser Ser His Gln Thr Gly Ile Pro Ala Arg Gly Ser His
            180                 185                 190

Tyr Ile Ala Asn Asn Lys Lys Met
            195                 200
```

<210> SEQ ID NO 11
<211> LENGTH: 200
<212> TYPE: PRT
<213> ORGANISM: Artificial Sequence
<220> FEATURE:
<223> OTHER INFORMATION: Modified CNTF

<400> SEQUENCE: 11

```
Met Ala Phe Thr Glu His Ser Pro Leu Thr Pro His Arg Arg Asp Leu
  1               5                  10                  15

Cys Ser Arg Ser Ile Trp Leu Ala Arg Lys Ile Arg Ser Asp Leu Thr
             20                  25                  30

Ala Leu Met Glu Ser Tyr Val Lys His Gln Gly Leu Asn Lys Asn Ile
         35                  40                  45

Asn Leu Asp Ser Val Asp Gly Val Pro Val Ala Ser Thr Asp Arg Trp
 50                  55                  60

Ser Glu Met Thr Glu Ala Glu Arg Leu Gln Glu Asn Leu Gln Ala Tyr
 65                  70                  75                  80

Arg Thr Phe His Val Leu Leu Ala Arg Leu Leu Glu Asp Gln Gln Val
                 85                  90                  95

His Phe Thr Pro Thr Glu Gly Asp Phe His Gln Ala Ile His Thr Leu
            100                 105                 110

Leu Leu Gln Val Ala Ala Phe Ala Tyr Gln Ile Glu Glu Leu Met Ile
        115                 120                 125

Leu Leu Glu Tyr Lys Ile Pro Arg Asn Glu Ala Asp Gly Met Pro Ile
130                 135                 140

Asn Val Gly Asp Gly Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
                165                 170                 175

Arg Phe Ile Ser Ser His Gln Thr Gly Ile Pro Ala Arg Gly Ser His
            180                 185                 190

Tyr Ile Ala Asn Asn Lys Lys Met
        195                 200
```

<210> SEQ ID NO 12
<211> LENGTH: 200
<212> TYPE: PRT
<213> ORGANISM: Artificial Sequence
<220> FEATURE:
<223> OTHER INFORMATION: Modified CNTF

<400> SEQUENCE: 12

```
Met Ala Phe Thr Glu His Ser Pro Leu Thr Pro His Arg Arg Asp Leu
  1               5                  10                  15

Cys Ser Arg Ser Ile Trp Leu Ala Arg Lys Ile Arg Ser Asp Leu Thr
             20                  25                  30

Ala Leu Thr Glu Ser Tyr Val Lys His Gln Gly Leu Asn Lys Asn Ile
         35                  40                  45

Asn Leu Asp Ser Val Asp Gly Val Pro Val Ala Ser Thr Asp Arg Trp
 50                  55                  60

Ser Glu Met Thr Glu Ala Glu Arg Leu Gln Glu Asn Leu Gln Ala Tyr
 65                  70                  75                  80

Arg Thr Phe His Val Leu Leu Ala Arg Leu Leu Glu Asp Gln Gln Val
                 85                  90                  95

His Phe Thr Pro Thr Glu Gly Asp Phe His Gln Ala Ile His Thr Leu
```

```
                100             105             110
Leu Leu Gln Val Ala Ala Phe Ala Tyr Gln Ile Glu Glu Leu Met Ile
            115                 120                 125

Leu Leu Glu Tyr Lys Ile Pro Arg Asn Glu Ala Asp Gly Met Pro Ile
    130                 135                 140

Asn Val Gly Asp Gly Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
                165                 170                 175

Arg Phe Ile Ser Ser His Gln Thr Gly Ile Pro Ala Arg Gly Ser His
            180                 185                 190

Tyr Ile Ala Asn Asn Lys Lys Met
        195                 200

<210> SEQ ID NO 13
<211> LENGTH: 200
<212> TYPE: PRT
<213> ORGANISM: Artificial Sequence
<220> FEATURE:
<223> OTHER INFORMATION: Modified CNTF

<400> SEQUENCE: 13

Met Ala Phe Thr Glu His Ser Pro Leu Thr Pro His Arg Arg Asp Leu
1               5                   10                  15

Cys Ser Arg Ser Ile Trp Leu Ala Arg Lys Ile Arg Ser Asp Leu Thr
            20                  25                  30

Ala Leu Thr Glu Ser Tyr Val Lys His Gln Gly Leu Asn Lys Asn Ile
        35                  40                  45

Asn Leu Asp Ser Val Asp Gly Met Pro Val Ala Ser Thr Asp Gln Trp
    50                  55                  60

Ser Glu Met Thr Glu Ala Glu Arg Leu Gln Glu Asn Leu Gln Ala Tyr
65                  70                  75                  80

Arg Thr Phe His Val Leu Leu Ala Arg Leu Leu Glu Asp Gln Gln Val
                85                  90                  95

His Phe Thr Pro Thr Glu Gly Asp Phe His Gln Ala Ile His Thr Leu
            100                 105                 110

Leu Leu Gln Val Ala Ala Phe Ala Tyr Gln Ile Glu Glu Leu Met Ile
            115                 120                 125

Leu Leu Glu Tyr Lys Ile Pro Arg Asn Glu Ala Asp Gly Met Pro Ile
    130                 135                 140

Asn Val Gly Asp Gly Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
                165                 170                 175

Arg Phe Ile Ser Ser His Gln Thr Gly Ile Pro Ala Arg Gly Ser His
            180                 185                 190

Tyr Ile Ala Asn Asn Lys Lys Met
        195                 200

<210> SEQ ID NO 14
<211> LENGTH: 200
<212> TYPE: PRT
<213> ORGANISM: Artificial Sequence
<220> FEATURE:
<223> OTHER INFORMATION: Modified CNTF

<400> SEQUENCE: 14
```

```
Met Ala Phe Thr Glu His Ser Pro Leu Thr Pro His Arg Arg Asp Leu
1               5                   10                  15

Cys Ser Arg Ser Ile Trp Leu Ala Arg Lys Ile Arg Ser Asp Leu Thr
            20                  25                  30

Ala Leu Thr Glu Ser Tyr Val Lys His Gln Gly Leu Asn Lys Asn Ile
            35                  40                  45

Asn Leu Asp Ser Val Asp Gly Val Pro Val Ala Ser Thr Asp Gln Trp
        50                  55                  60

Ser Glu Leu Thr Glu Ala Glu Arg Leu Gln Glu Asn Leu Gln Ala Tyr
65                  70                  75                  80

Arg Thr Phe His Val Leu Leu Ala Arg Leu Leu Glu Asp Gln Gln Val
                85                  90                  95

His Phe Thr Pro Thr Glu Gly Asp Phe His Gln Ala Ile His Thr Leu
                100                 105                 110

Leu Leu Gln Val Ala Ala Phe Ala Tyr Gln Ile Glu Glu Leu Met Ile
            115                 120                 125

Leu Leu Glu Tyr Lys Ile Pro Arg Asn Glu Ala Asp Gly Met Pro Ile
        130                 135                 140

Asn Val Gly Asp Gly Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
                165                 170                 175

Arg Phe Ile Ser Ser His Gln Thr Gly Ile Pro Ala Arg Gly Ser His
                180                 185                 190

Tyr Ile Ala Asn Asn Lys Lys Met
            195                 200

<210> SEQ ID NO 15
<211> LENGTH: 200
<212> TYPE: PRT
<213> ORGANISM: Artificial Sequence
<220> FEATURE:
<223> OTHER INFORMATION: Modified CNTF

<400> SEQUENCE: 15

Met Ala Phe Thr Glu His Ser Pro Leu Thr Pro His Arg Arg Asp Leu
1               5                   10                  15

Cys Ser Arg Ser Ile Trp Leu Ala Arg Lys Ile Arg Ser Asp Leu Thr
            20                  25                  30

Ala Leu Thr Glu Ser Tyr Val Lys His Gln Gly Leu Asn Lys Asn Ile
            35                  40                  45

Asn Leu Asp Ser Ala Asp Gly Met Pro Val Ala Ser Thr Asp Arg Trp
        50                  55                  60

Ser Glu Leu Thr Glu Ala Glu Arg Leu Gln Glu Asn Leu Gln Ala Tyr
65                  70                  75                  80

Arg Thr Phe His Val Leu Leu Ala Arg Leu Leu Glu Asp Gln Gln Val
                85                  90                  95

His Phe Thr Pro Thr Glu Gly Asp Phe His Gln Ala Ile His Thr Leu
                100                 105                 110

Leu Leu Gln Val Ala Ala Phe Ala Tyr Gln Ile Glu Glu Leu Met Ile
            115                 120                 125

Leu Leu Glu Tyr Lys Ile Pro Arg Asn Glu Ala Asp Gly Met Pro Ile
        130                 135                 140

Asn Val Gly Asp Gly Gly Leu Phe Glu Lys Lys Leu Trp Gly Leu Lys
145                 150                 155                 160
```

-continued

```
Val Leu Gln Glu Leu Ser Gln Trp Thr Val Arg Ser Ile His Asp Leu
                165                 170                 175

Arg Phe Ile Ser Ser His Gln Thr Gly Ile Pro Ala Arg Gly Ser His
            180                 185                 190

Tyr Ile Ala Asn Asn Lys Lys Met
        195                 200

<210> SEQ ID NO 16
<211> LENGTH: 184
<212> TYPE: PRT
<213> ORGANISM: Artificial Sequence
<220> FEATURE:
<223> OTHER INFORMATION: Ax-15 protein

<400> SEQUENCE: 16

Ala Phe Thr Glu His Ser Pro Leu Thr Pro His Arg Arg Asp Leu Ala
 1               5                  10                  15

Ser Arg Ser Ile Trp Leu Ala Arg Lys Ile Arg Ser Asp Leu Thr Ala
            20                  25                  30

Leu Thr Glu Ser Tyr Val Lys His Gln Gly Leu Asn Lys Asn Ile Asn
        35                  40                  45

Leu Asp Ser Ala Asp Gly Met Pro Val Ala Ser Thr Asp Arg Trp Ser
    50                  55                  60

Glu Leu Thr Glu Ala Glu Arg Leu Gln Glu Asn Leu Gln Ala Tyr Arg
65                  70                  75                  80

Thr Phe His Val Leu Leu Ala Arg Leu Leu Glu Asp Gln Gln Val His
                85                  90                  95

Phe Thr Pro Thr Glu Gly Asp Phe His Gln Ala Ile His Thr Leu Leu
            100                 105                 110

Leu Gln Val Ala Ala Phe Ala Tyr Gln Ile Glu Glu Leu Met Ile Leu
        115                 120                 125

Leu Glu Tyr Lys Ile Pro Arg Asn Glu Ala Asp Gly Met Pro Ile Asn
    130                 135                 140

Val Gly Asp Gly Gly Leu Phe Glu Lys Lys Leu Trp Gly Leu Lys Val
145                 150                 155                 160

Leu Gln Glu Leu Ser Gln Trp Thr Val Arg Ser Ile His Asp Leu Arg
                165                 170                 175

Phe Ile Ser Ser His Gln Thr Gly
            180

<210> SEQ ID NO 17
<211> LENGTH: 185
<212> TYPE: PRT
<213> ORGANISM: Artificial Sequence
<220> FEATURE:
<223> OTHER INFORMATION: Methionine+ Ax-15 protein

<400> SEQUENCE: 17

Met Ala Phe Thr Glu His Ser Pro Leu Thr Pro His Arg Arg Asp Leu
 1               5                  10                  15

Ala Ser Arg Ser Ile Trp Leu Ala Arg Lys Ile Arg Ser Asp Leu Thr
            20                  25                  30

Ala Leu Thr Glu Ser Tyr Val Lys His Gln Gly Leu Asn Lys Asn Ile
        35                  40                  45

Asn Leu Asp Ser Ala Asp Gly Met Pro Val Ala Ser Thr Asp Arg Trp
    50                  55                  60

Ser Glu Leu Thr Glu Ala Glu Arg Leu Gln Glu Asn Leu Gln Ala Tyr
65                  70                  75                  80
```

```
Arg Thr Phe His Val Leu Leu Ala Arg Leu Leu Glu Asp Gln Gln Val
                 85                  90                  95

His Phe Thr Pro Thr Glu Gly Asp Phe His Gln Ala Ile His Thr Leu
            100                 105                 110

Leu Leu Gln Val Ala Ala Phe Ala Tyr Gln Ile Glu Glu Leu Met Ile
        115                 120                 125

Leu Leu Glu Tyr Lys Ile Pro Arg Asn Glu Ala Asp Gly Met Pro Ile
    130                 135                 140

Asn Val Gly Asp Gly Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
                165                 170                 175

Arg Phe Ile Ser Ser His Gln Thr Gly
            180                 185

<210> SEQ ID NO 18
<211> LENGTH: 21
<212> TYPE: DNA
<213> ORGANISM: Artificial Sequence
<220> FEATURE:
<223> OTHER INFORMATION: Primer

<400> SEQUENCE: 18
acggtaagct tggaggttct c                                           21

<210> SEQ ID NO 19
<211> LENGTH: 48
<212> TYPE: DNA
<213> ORGANISM: Artificial Sequence
<220> FEATURE:
<223> OTHER INFORMATION: Primer

<400> SEQUENCE: 19
tctatctggc tagcaaggaa gattcgttca gacctgactg ctcttacg              48

<210> SEQ ID NO 20
<211> LENGTH: 69
<212> TYPE: DNA
<213> ORGANISM: Artificial Sequence
<220> FEATURE:
<223> OTHER INFORMATION: Primer

<400> SEQUENCE: 20
aaggtacgat aagcttggag gttctcttgg agtcgctctg cctcagtcag ctcactccaa 60
cgatcagtg                                                         69

<210> SEQ ID NO 21
<211> LENGTH: 21
<212> TYPE: DNA
<213> ORGANISM: Artificial Sequence
<220> FEATURE:
<223> OTHER INFORMATION: Primer

<400> SEQUENCE: 21
tctatctggc tagcaaggaa g                                           21

<210> SEQ ID NO 22
<211> LENGTH: 27
<212> TYPE: DNA
<213> ORGANISM: Artificial Sequence
<220> FEATURE:
<223> OTHER INFORMATION: Primer
```

```
<400> SEQUENCE: 22
ccagatagag gagttaatga tactcct                                              27

<210> SEQ ID NO 23
<211> LENGTH: 47
<212> TYPE: DNA
<213> ORGANISM: Artificial Sequence
<220> FEATURE:
<223> OTHER INFORMATION: Primer

<400> SEQUENCE: 23
gcgtcggccg cggaccacgc tcattaccca gtctgtgaga agaaatg                        47
```